US012087431B2

(12) United States Patent
Urness et al.

(10) Patent No.: US 12,087,431 B2
(45) Date of Patent: Sep. 10, 2024

(54) MEDICAL IMAGING UPGRADES PROVIDING IMPROVED DATA QUALITY AND ACCESSIBILITY

(71) Applicant: Exo Imaging, Inc., Redwood City, CA (US)

(72) Inventors: Mark Urness, Pewaukee, WI (US); Drake Guenther, Hillsborough, CA (US); Michael Ross, Fruit Heights, UT (US)

(73) Assignee: Exo Imaging, Inc., Santa Clara, CA (US)

( * ) Notice: Subject to any disclaimer, the term of this patent is extended or adjusted under 35 U.S.C. 154(b) by 320 days.

(21) Appl. No.: 17/506,459

(22) Filed: Oct. 20, 2021

(65) Prior Publication Data

US 2023/0122851 A1    Apr. 20, 2023

(51) Int. Cl.
   *G16H 30/40*    (2018.01)
   *G06F 16/215*   (2019.01)
   *G16H 15/00*    (2018.01)
   *G16H 30/20*    (2018.01)

(52) U.S. Cl.
   CPC .......... *G16H 30/40* (2018.01); *G06F 16/215* (2019.01); *G16H 15/00* (2018.01); *G16H 30/20* (2018.01)

(58) Field of Classification Search
   CPC ........ G16H 30/40; G16H 15/00; G16H 30/20; G06F 16/215
   See application file for complete search history.

(56) References Cited

U.S. PATENT DOCUMENTS

2018/0189447 A1*   7/2018   Khatri .................. G06K 7/1099
2019/0347387 A1*  11/2019   Woodward ............. G16H 15/00

OTHER PUBLICATIONS

PCT/US2021/055890 International Search Report and Written Opinion dated Jan. 26, 2022.
Co-pending U.S. Appl. No. 29/830,792, inventors Pupo; Michael et al., filed Mar. 15, 2022.
Co-pending U.S. Appl. No. 29/830,797, inventors Pupo; Michael et al., filed Mar. 15, 2022.
Co-pending U.S. Appl. No. 29/830,798, inventors Pupo; Michael et al., filed Mar. 15, 2022.
Co-pending U.S. Appl. No. 29/830,799, inventors Pupo; Michael et al., filed Mar. 15, 2022.

(Continued)

*Primary Examiner* — John J Lee
(74) *Attorney, Agent, or Firm* — Morgan, Lewis & Bockius LLP

(57) ABSTRACT

Described are platforms, systems, and methods for efficient collection and processing of patient medical data, including medical images, videos, or multiframes and patient biographical information. Provision of a mobile device application comprising a scanning module configured to acquire patient biographical information and interface directly or indirectly with a network node provided with medical images obtained from a medical imaging system can decrease data loss in clinical settings, in various embodiments. Improvement of existing medical imaging systems using mobile device applications and/or system configurations described herein can significantly increase efficiency of data entry and analysis, in various embodiments.

19 Claims, 5 Drawing Sheets

(56) References Cited

OTHER PUBLICATIONS

Co-pending U.S. Appl. No. 29/830,801, inventors Pupo; Michael et al., filed Mar. 15, 2022.
Co-pending U.S. Appl. No. 29/830,802, inventors Pupo; Michael et al., filed Mar. 15, 2022.
Co-pending U.S. Appl. No. 29/830,804, inventors Pupo; Michael et al., filed Mar. 15, 2022.

* cited by examiner

MEDICAL IMAGING UPGRADES PROVIDING IMPROVED DATA QUALITY AND ACCESSIBILITY

BACKGROUND

Maintaining fidelity between clinical diagnostic data and patient biographical information is critical to high-quality patient care. Should clinical diagnostic data become disassociated with the proper patient profile, for example, through failure to associate all or a portion of the clinical diagnostic data with a patient profile or through misassociation of clinical diagnostic data with an incorrect patient profile, the need to reacquire all or a portion of the clinical data and/or the possibility of incorrect diagnoses and/or prescribed treatments becomes a major concern.

Traditionally, clinical diagnostic data (e.g., diagnostic medical imaging data) has been acquired using a dedicated medical imaging device and manually associated with a given patient's clinical profile. Even systems that may be connected to a local electronic database often require manual entry of patient information to effectively label clinical data and/or manual transfer of clinical diagnostic data to a specific target data storage location. Failure to perform either of these tasks successfully each time data is collected can lead to data loss and/or data corruption, which can require costly and unnecessary troubleshooting or data replacement and can adversely impact quality of patient care.

SUMMARY

Many existing models of medical equipment used for clinical data acquisition (e.g., medical imaging devices, such as ultrasound imaging devices, magnetic resonance imaging (MRI) scanners, radiographic imagers (e.g., X-ray machines), positron emission tomography scanners, and computed tomography (CT) scanners) lack a means for automatic modification of clinical diagnostic data files to include a patient's clinical data profile (e.g., medical history record) and/or automatic integration with a healthcare provider's clinical workflow system. In many cases, patient identification information must be manually entered into the clinical data acquisition system (e.g., the medical imaging system) during or after a data acquisition session. Modification of the stored clinical diagnostic data to include a patient's medical history record and/or integration of acquired clinical diagnostic data with a healthcare provider's workflow system represent a second set of logistical bottlenecks, which existing clinical data acquisitions systems are often ill-equipped to handle. In each of these cases, the transposition, omission, or incorrect entry of a single numeric or alphanumeric character of a patient identifier (e.g., a patient name, patient date of birth, patient gender, patient address, medical history number, medical record number, or medical insurance number), or medical code (such as a current procedural terminology (CPT) code or a Healthcare Common Procedure Coding System (HCPCS) code) can severely hinder the ability of healthcare providers to access or use acquired clinical data. In cases where patient identifier information may be difficult to locate, hard to read, or challenging to input at the time of data acquisition (e.g., during time-critical conditions, such as emergency medical conditions, or situations where data acquisition is performed before a patient is admitted to a medical facility), input of patient identifier(s) and/or collation of patient identifier(s) with clinical data may be especially prone to error.

Additionally, medical equipment used for data acquisition are often exceedingly expensive to replace or upgrade, which can present logistical challenges for integration of existing medical at a medical care facility with newer, potentially incompatible data management systems and/or peripheral equipment associated with a data acquisition system. In many cases, existing medical data acquisition systems (e.g., existing models of medical imaging systems) do not comprise an integrated means to facilitate recordation of patient identification information (e.g., patient identifier(s)), which can lead to costly and potentially dangerous breakdowns in clinical workflow arising from continued use of such data acquisition systems or the integration of such a data acquisition system with a newer system implemented in the same clinical setting. For example, a medical care facility adding a new MRI scanner having a specific patient information input mechanism may experience significant and persistent difficulty in the continued use of an older model of MIl scanner at the facility, manual and potentially customized systems and protocols may be required to rectify the ongoing use of both machines (for example, if data acquisition is performed on the same patient using each scanner during the same visit to the medical care facility).

Employing platforms, systems, and methods described herein, which can comprise the use of a healthcare provider application having a module for acquiring patient identifier(s), for instance, when installed on a mobile device, can circumvent many of the problems described herein that may be inherent in or emergent from the use of medical data acquisition systems (e.g., medical imaging systems). In some cases, platforms, systems, and methods described herein can be used to upgrade a medical imaging system, for example, to include a scanner capable of patient identifier acquisition. In some cases, platforms, system, and methods described herein can be used to create combined patient data records, for instance, which can comprise patient identifier(s), diagnostic data (e.g., comprising medical imaging data), and/or existing medical record information. Platforms, systems, and methods described herein can improve data quality (e.g., by decreasing data loss and increasing capacity for data recordation) and/or efficiency of data acquisition processes.

In one aspect, disclosed herein are platforms providing an upgraded medical imaging system, the platform comprising: an electronic medical records system comprising a data store comprising a plurality of patient electronic medical records (EMRs); an existing medical imaging system; a mobile device provided with a healthcare provider application comprising: a scanning module configured to acquire a unique patient identifier associated with a patient; an accessibility module configured to provide a healthcare provider accessibility display comprising the unique patient identifier on a screen of the mobile device; and a front-end data quality module configured to transmit the unique patient identifier over a network; and a server provided with an interface application comprising: a back-end data quality module configured to receive the unique patient identifier over the network; an imaging session module configured to perform operations comprising: create an imaging session record using the unique patient identifier; receive at least one medical image from the existing medical imaging system; and create a medical imaging record based at least in part on the unique patient identifier and the at least one medical image; and an EMR module configured to persist the medical imaging record to the electronic medical record for the patient at the data store of the electronic medical records system. In some embodiments, the data store comprises a database server. In other embodiments, the data store comprises a cloud data store. In various embodiments, the existing medical imaging system comprises an ultrasound device, an x-ray radiography device, a magnetic resonance imaging device, an endoscopy device, a thermography device, a photography device, an X-ray computed tomography (CT) device, a positron emission tomography (PET) device, a single-photon emission computed tomography (SPECT) device, a photoacoustic imaging device, or a combination thereof. In further embodiments, the existing medical imaging system is DICOM-enabled. In some embodiments, the healthcare provider application comprises a front-end medical imaging workflow application. In further embodiments, the healthcare provider application is implemented as a native mobile application. In various embodiments, the unique patient identifier comprises a text string, a number, a biometric feature of the patient, a linear barcode, a 2D barcode, or a combination thereof. In some embodiments, the healthcare provider application acquires the unique patient identifier using a camera of the mobile device. In some embodiments, the healthcare provider application further comprises a healthcare provider sign-in module configured to verify the identity of a healthcare provider operating the healthcare provider application. In further embodiments, a module of the interface application is configured to transmit the medical imaging record to the healthcare provider. In still further embodiments, a module of the interface application is configured to transmit the medical imaging record to a dedicated communication server. In some embodiments, a module of the interface application is configured to use the unique patient identifier to retrieve patient information from the electronic medical records system. In some embodiments, the platform further comprises a back-end medical imaging workflow application. In further embodiments, the back-end medical imaging workflow application is implemented as a cloud application. In some embodiments, the existing medical imaging system does not have access to the unique patient identifier. In some embodiments, neither the mobile device nor the healthcare provider application communicates directly with the existing medical imaging system. In some embodiments, the platform is configured to provide the upgraded medical imaging system without modifying the existing medical imaging system. In some embodiments, the front-end data quality module is further configured to initiate an EMR query. In further embodiments, initiating an EMR query comprises transmitting an EMR query initiation signal to the server. In further embodiments, the interface application is configured to compare a timestamp of the unique patient identifier and a timestamp of the at least one medical image.

In another aspect, disclosed herein are computer-implemented methods for improved data quality of an existing medical imaging device comprising: acquiring a unique patent identifier associated with a patient utilizing a healthcare provider application on a mobile device; transmitting, by the healthcare provider application, the unique patient identifier over a network to an interface application on a server; receiving, at the interface application, at least one medical image from the existing medical imaging system via the network; creating a medical imaging record based at least in part on the unique patient identifier and the at least one medical image; and persisting the medical imaging record to a data store of an electronic medical record for the patient. In some embodiments, the method further comprises creating an imaging session record using the unique patient identifier. In some embodiments, the data store comprises a database server. In other embodiments, the data store comprises a cloud data store. In some embodiments, the method further comprises providing a healthcare provider accessibility display comprising the unique patient identifier on a screen of the mobile device. In various embodiments, the existing medical imaging system comprises an ultrasound device, an x-ray radiography device, a magnetic resonance imaging device, an endoscopy device, a thermography device, a photography device, an X-ray computed tomography (CT) device, a positron emission tomography (PET) device, a single-photon emission computed tomography (SPECT) device, a photoacoustic imaging device, or a combination thereof. In further embodiments, the existing medical imaging system is DICOM-enabled. In some embodiments, the healthcare provider application is implemented as a native mobile application on the mobile device. In various embodiments, the unique patient identifier comprises a text string, a number, a biometric feature of the patient, a linear barcode, a 2D barcode, or a combination thereof. In some embodiments, the healthcare provider application acquires the unique patient identifier using a camera of the mobile device. In some embodiments, the method further comprises verifying the identity of a healthcare provider operating the healthcare provider application. In some embodiments, the existing medical imaging system does not have access to the unique patient identifier. In some embodiments, neither the mobile device nor the healthcare provider application communicates directly with the existing medical imaging system. In some embodiments, the method further comprises transmitting the medical imaging record to a healthcare provider. In further embodiments, the medical imaging record is transmitted from the interface application to a communication server. In some embodiments, the method further comprises retrieving patient information from the electronic medical records system using the unique patient identifier. In some embodiments, the method provides the upgraded medical imaging system without modifying the existing medical imaging system. In some embodiments, the method further comprises generating an EMR query initiation signal at the healthcare provider application. In further embodiments, the method further comprises transmitting the EMR query to the electronic medical records system via the server.

In another aspect, disclosed herein are mobile computing devices comprising: at least one processor, a memory, a display, a network interface, and instructions executable by the at least one processor to provide a healthcare provider application comprising: a scanning module configured to acquire a unique patient identifier associated with a patient; an accessibility module configured to provide a healthcare provider accessibility interface comprising the unique patient identifier on the display; and a data quality module configured to transmit the unique patient identifier over a network, utilizing the network interface, to a server comprising an interface application for integration with at least one medical image generated by a medical imaging system to create a medical imaging record; wherein the transmitted unique patient identifier and the medical imaging record is persisted to an electronic medical record for the patient at a data store of an electronic medical records system. In some embodiments, the healthcare provider application is implemented as a mobile native application. In other embodiments, the healthcare provider application is implemented as a mobile web application. In some embodiments, the mobile computing device further comprises a camera. In further embodiments, the scanning module of the healthcare provider application acquires the unique patient identifier utilizing the camera of the mobile computing device. In various embodiments, the unique patient identifier comprises a text string, a number, a biometric feature of the patient, a linear barcode, a 2D barcode, or a combination thereof. In some embodiments, the healthcare provider accessibility interface comprises an audio presentation of the unique patient identifier. In some embodiments, the healthcare provider accessibility interface comprises an enlarged, high contrast presentation of the unique patient identifier. In some embodiments, the network interface comprises a wireless network interface controller and the network comprises a wireless network. In some embodiments, the electronic medical records system comprises a plurality of patient electronic medical records (EMRs). In various embodiments, the medical imaging system comprises an ultrasound device, an x-ray radiography device, a magnetic resonance imaging device, an endoscopy device, a thermography device, a photography device, an X-ray computed tomography (CT) device, a positron emission tomography (PET) device, a single-photon emission computed tomography (SPECT) device, a photoacoustic imaging device, or a combination thereof. In further embodiments, the medical imaging system is DICOM-enabled. In some embodiments, the healthcare provider application further comprises a healthcare provider sign-in module configured to verify the identity of a healthcare provider operating the healthcare provider application. In some embodiments, the healthcare provider application further comprises a medical imaging workflow interface. In some embodiments, the healthcare provider application further comprises an EMR query module configured to initiate an EMR query for the patient. In further embodiments, initiating the EMR query comprises transmitting an EMR query initiation signal to the server. In some embodiments, the medical imaging system does not have access to the unique patient identifier. In some embodiments, neither the mobile device nor the healthcare provider application communicates directly with the medical imaging system.

BRIEF DESCRIPTION OF THE DRAWINGS

A better understanding of the features and advantages of the present subject matter will be obtained by reference to the following detailed description that sets forth illustrative embodiments and the accompanying drawings of which.

DETAILED DESCRIPTION

Figure 1:
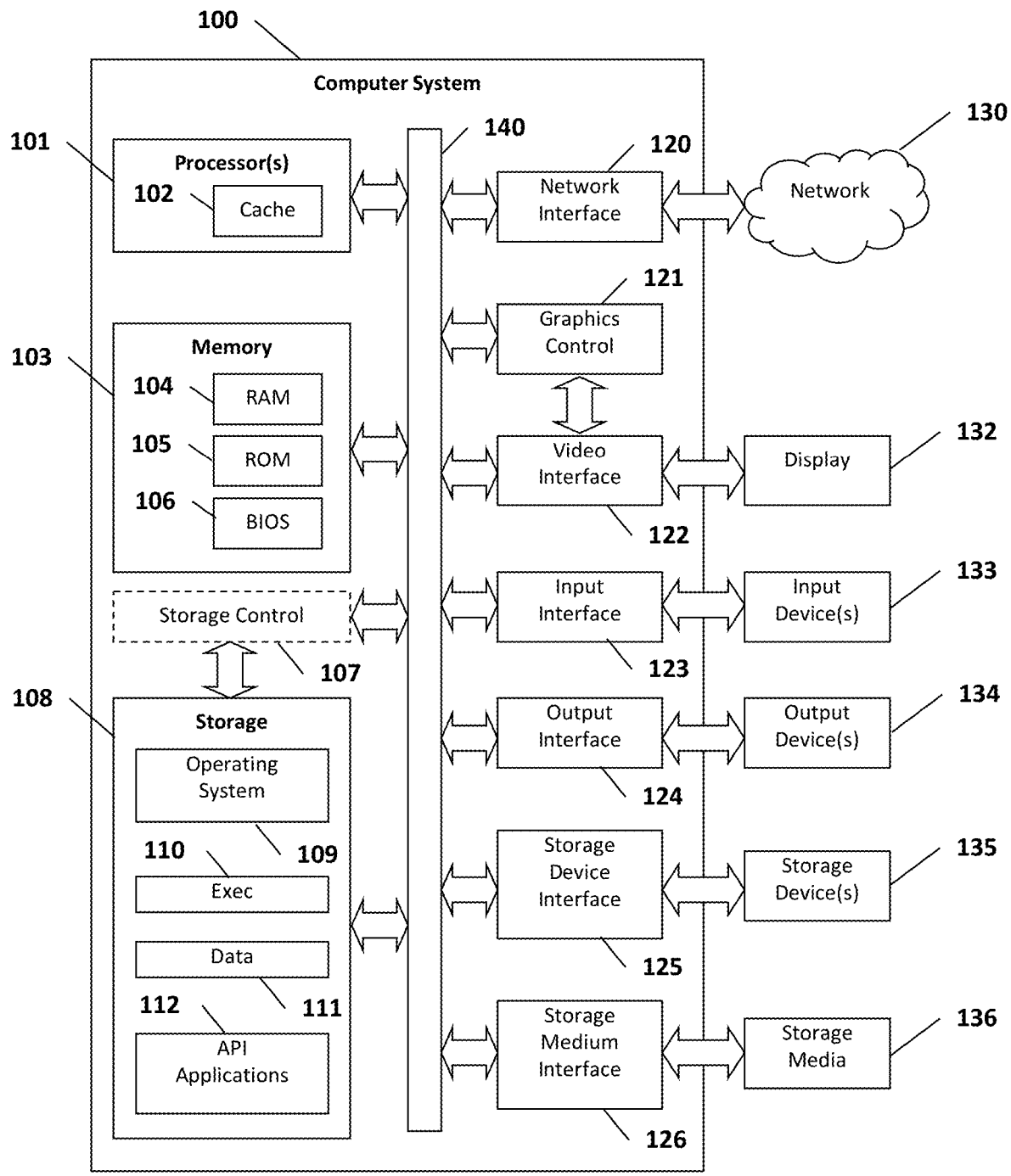
FIG. 1 shows a non-limiting example of a computing device; in this case, a device with one or more processors, memory, storage, and a network interface.

Described herein, in certain embodiments, are platforms providing an upgraded medical imaging system, the platform comprising: an electronic medical records system comprising a data store comprising a plurality of patient electronic medical records (EMRs); an existing medical imaging system; a mobile device provided with a healthcare provider application comprising: a scanning module configured to acquire a unique patient identifier associated with a patient; an accessibility module configured to provide a healthcare provider accessibility display comprising the unique patient identifier on a screen of the mobile device; and a front-end data quality module configured to transmit the unique patient identifier over a network; and a server provided with an interface application comprising: a back-end data quality module configured to receive the unique patient identifier over the network; an imaging session module configured to perform operations comprising: create an imaging session record using the unique patient identifier; receive at least one medical image from the existing medical imaging system; and create a medical imaging record based at least in part on the unique patient identifier and the at least one medical image; and an EMR module configured to persist the medical imaging record to the electronic medical record for the patient at the data store of the electronic medical records system.

Also described herein, in certain embodiments, are computer-implemented methods for improved data quality of an existing medical imaging device comprising: acquiring a unique patent identifier associated with a patient utilizing a healthcare provider application on a mobile device; transmitting, by the healthcare provider application, the unique patient identifier over a network to an interface application on a server; receiving, at the interface application, at least one medical image from the existing medical imaging system via the network; creating a medical imaging record based at least in part on the unique patient identifier and the at least one medical image; and persisting the medical imaging record to a data store of an electronic medical record for the patient.

Also described herein, in certain embodiments, are mobile computing devices comprising: at least one processor, a memory, a display, a network interface, and instructions executable by the at least one processor to provide a healthcare provider application comprising: a scanning module configured to acquire a unique patient identifier associated with a patient; an accessibility module configured to provide a healthcare provider accessibility interface comprising the unique patient identifier on the display; and a data quality module configured to transmit the unique patient identifier over a network, utilizing the network interface, to a server comprising an interface application for integration with at least one medical image generated by a medical imaging system to create a medical imaging record; wherein the transmitted unique patient identifier and the medical imaging record is persisted to an electronic medical record for the patient at a data store of an electronic medical records system.

Overview

Figure 2:
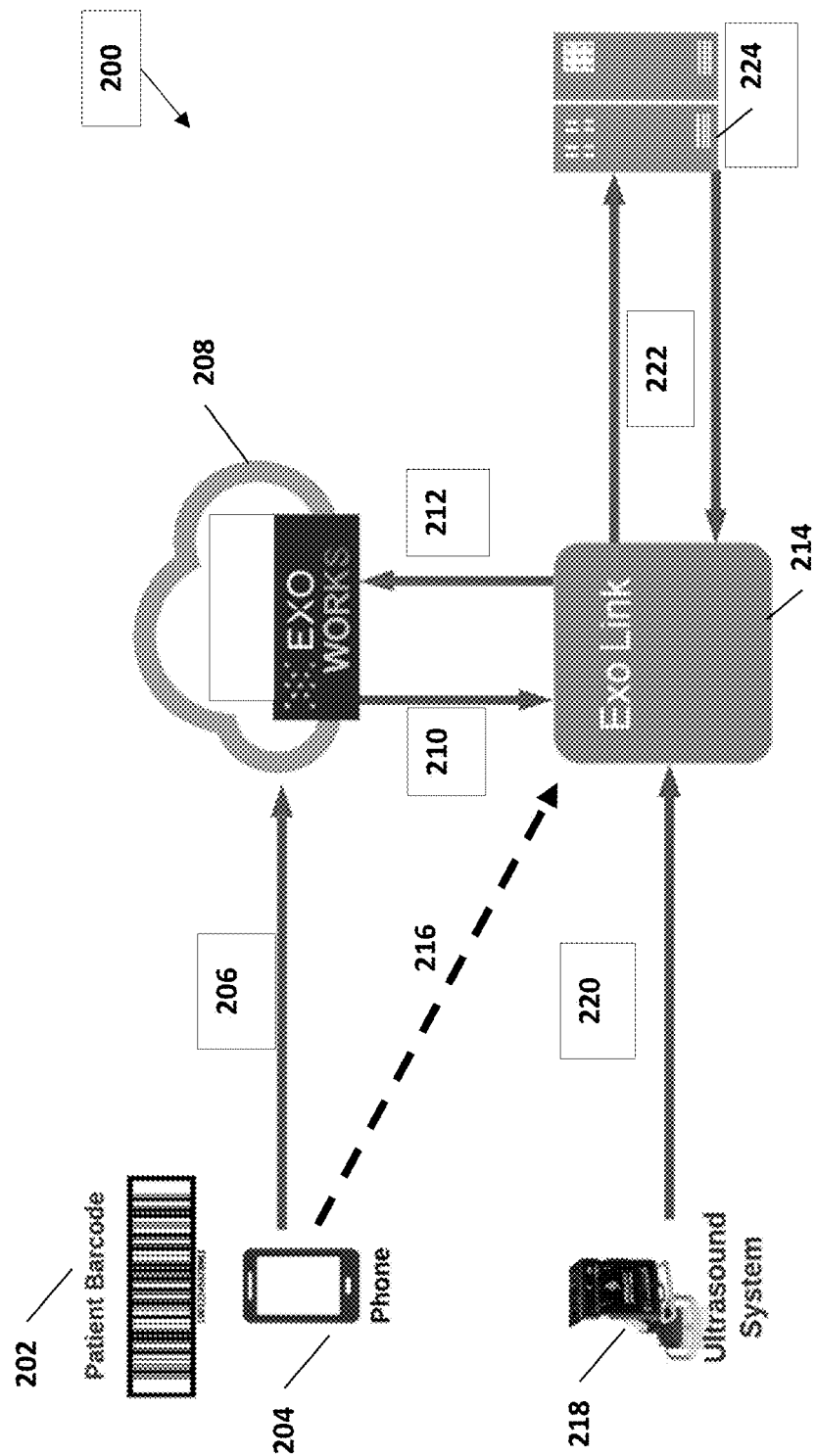
FIG. 2 shows a non-limiting example of an overall platform organizational diagram; in this case, an organizational diagram showing direct and indirect integration of a mobile device comprising a healthcare provider application with a server-based medical data acquisition system.

FIG. 2 shows a schematic representation of devices, platforms 200, and systems 200 that can be useful in acquisition of medical diagnostic data, acquisition of patient identifier data, creation or modification of patient medical records, and/or upgrading existing medical equipment, such as medical imaging systems, e.g., as described herein. A mobile device 204 comprising a mobile device application (e.g., a healthcare provider application) can be used to acquire one or more patient identifiers 202 (e.g., comprising a patient barcode), for example using a camera or scanner of the mobile device 204. The one or more patient identifiers 202 can be optionally converted from a first format into a second format (e.g., from an image file into a text string or file) using the mobile device application. The one or more patient identifiers 202 (e.g., in a format native to the acquisition method or modified to a second format) can be transmitted by the mobile device application to a virtual (e.g., cloud-based) server 208 via a wired or wireless network connection, which may comprise a telecommunications network. The virtual server 208 can transmit the one or more patient identifiers to an interface application instantiated on a virtual or physical server 214 (see, e.g., FIG. 2 at 210). In some cases, the virtual or physical server 214 can transmit information (e.g., comprising status and/or connection information) to the virtual server 208 (see, e.g., FIG. 2 at 212). In some cases, the one or more patient identifiers 202 can be transmitted by the mobile device application directly to an interface application instantiated on a virtual or physical server 214 directly (see, e.g., FIG. 2 at 216. The interface application instantiated on the virtual or physical server 214 can be configured to receive medical diagnostic data (e.g., comprising one or more medical images, video, or multiframes) from a medical imaging system 218 (e.g., an existing medical imaging system). In some cases, the interface application instantiated on the server 214 can combine the one or more patient identifiers and the medical diagnostic data into a medical imaging record. In some cases, the interface application of the server 214 can be configured to transmit the medical imaging record to a data store of an electronic medical record system 224 (EMR system) (see, e.g., FIG. 2 at 222). In some cases, the interface application instantiated on the server 214 can be configured to receive an electronic medical record (EMR) (e.g., that is associated with the one or more patient identifiers) from the EMR system 224, for example, subsequent to relay of an EMR query from the interface application to the EMR system 224 (e.g., as a result of an EMR query initiation signal transmitted to the interface application by the mobile device application), as described herein. In some cases, the interface application instantiated on the server 214 can be configured to transmit all or a portion of the information comprising the EMR to the virtual server 208 (see, e.g., FIG. 2 at 212) and/or to the mobile device application instantiated on the mobile device 204.

Figure 3:
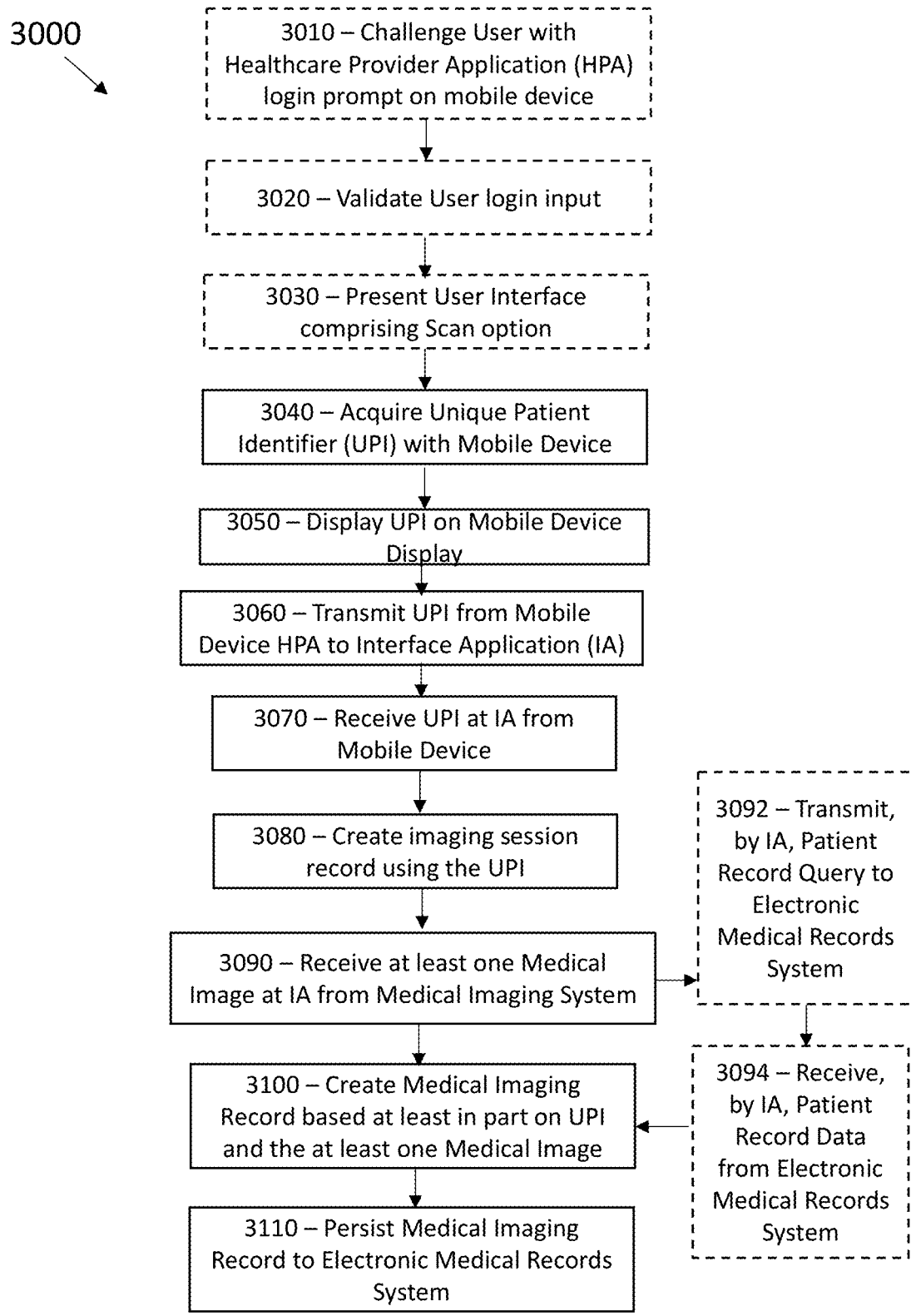
FIG. 3 shows a first example of a process flow chart, in accordance with embodiments; in this case, a process flow chart showing a first method for improved data quality of a medical imaging device.
Figure 4:
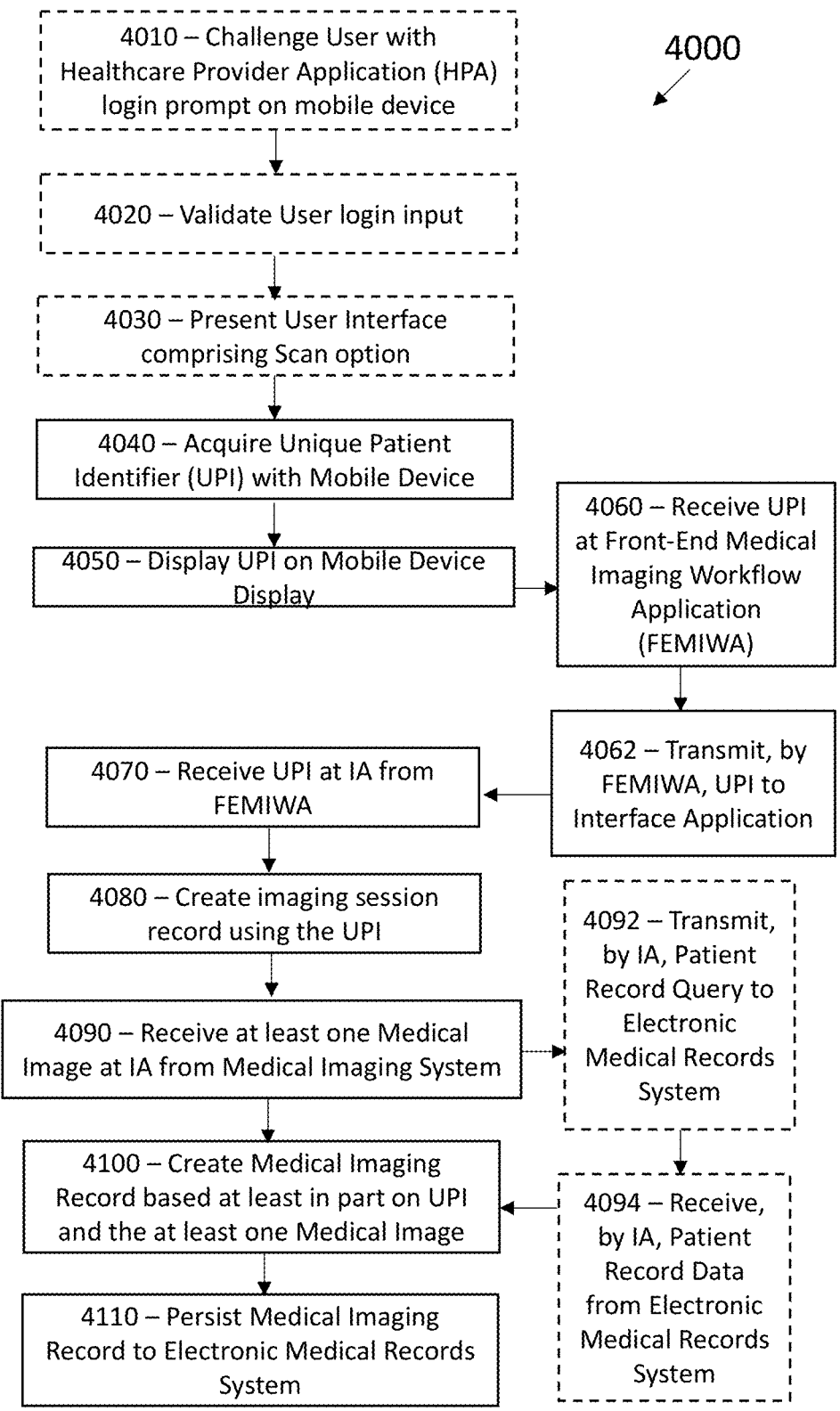
FIG. 4 shows a second example of a process flow chart, in accordance with embodiments; in this case, a process flow chart showing a second method for improved data quality of a medical imaging device.

FIG. 3 and FIG. 4 show a flowcharts of embodiments of methods 3000 and 4000, respectively, which can be useful in acquisition of medical diagnostic data, acquisition of patient identifier data, creation or modification of patient medical records, and/or upgrading existing medical equipment, such as medical imaging systems, e.g., as described herein. In some cases, a mobile device application (e.g., a Healthcare Provider Application (HPA)) can present a user (e.g., a healthcare provider) with a login prompt, e.g., on a screen of the mobile device on which the mobile device application is instantiated, as shown at optional step 3010 and optional step 4010. A login challenge to a user can increase data security by verifying the identity of the user (e.g., an authorized user, such as a specific authorized healthcare provider). In some embodiment, successful validation of a user's login information after login challenge (e.g., as in steps 3020 and 3010 and as shown in steps 4020 and 4010) can also connect the subsequent mobile device application usage session with a specific user profile, which can be used to (e.g., automatically) access a specific set of patient data (e.g., from one or more electronic medical records and/or one or more previous medical imaging records) and/or connect to or coordinate with a specific set of medical imaging systems and/or a specific interface application (IA). In some cases, user login challenge and validation can be used to apply preferred settings related to a method, platform, or system described herein. For example, a method, platform, or system described herein may configured to access or interface with a wireless or telecommunication network, for example, to (e.g., automatically) send messages (e.g., comprising patient identifiers, medical diagnostic data, electronic medical records, medical imaging records, confirmation messages, session summary messages, or a combination thereof) to a telecommunication destination (e.g., an email account or voice mail) either automatically or upon input from the user during or after the usage session. In some cases, a method can include presenting a user interface (e.g., at step 3030 or step 4030), for example via a screen of the mobile device, as a result of successful validation (e.g., at step 3020 or step 4020) of login information provided by a user upon challenge (e.g., at step 3010 or step 4010). In some cases, presentation of a user interface can comprise application of user accessibility settings and preferences, as described herein (e.g., which may include adjusting display font, color, contrast, and/or application of speech-to-text functionalities). In some cases, presentation of a user interface can comprise presenting the user with options for functionalities of the platform, system, or method. For example, presentation of a user interface (e.g., as in step 3030) can comprise presenting a user interface that comprises a scan option (e.g., for initiating acquisition of patient identifier data, for instance, through the operation of a camera or scanner of the mobile device), a settings option (e.g., for adjusting or implementing accessibility functionalities), and/or an EMR query option (e.g., to allow a user to define and/or transmit an EMR query, for instance, by transmitting an EMR query initiation signal, as described herein). Methods 3000 and 4000 can comprise acquiring patient identifier data (e.g., comprising one or more unique patient identifiers (UPIs)), for instance by operating a camera or scanner of the mobile device in response to a command input by the user (e.g., as shown in step 3040 or step 4040).

Methods 3000 and 4000 can comprise displaying acquired patient identifier data on a mobile device display, which may comprise a screen (e.g., as shown in step 3050 or step 4050). Displaying the acquired patient identifier data to the user can improve data quality, e.g., by presenting the user with an opportunity to reacquire patient identifier data while the opportunity to do so is still at hand, for instance by allowing the user to examine the acquired patient identifier data against the original source of the patient identifier data. Furthermore, displaying the acquired patient identifier data to the user (e.g., as shown in step 3050 or step 4050) can improve the accessibility of an existing medical imaging system, which may lack a means for displaying acquired patient identifier data or which may comprise a display that lacks adequate display accessibility (e.g., wherein the display lacks the sufficient capability for adjusting font type, font size, color, contrast, and/or implementing other accessibility features, such as speech-to-text functionality). In some cases, patient identifier data (e.g., comprising one or more unique patient identifiers) can be manually entered into the mobile device (e.g., by a user), for example, via a display of the mobile device. In some cases, the display can be used to confirm patient identifier data manually entered into the mobile device (e.g., by a user).

A method 3000 can comprise transmitting patient identifier data (e.g., comprising one or more UPIs) directly from the mobile device application (e.g., the mobile device HPA) or a module thereof to an interface application (IA), which may be instantiated on a virtual or physical server, as described herein, for example, as shown in step 3060. In some cases, an interface application (IA) instantiated on a virtual or physical server can comprise a module (e.g., a back-end data quality module) configured to receive patient identifier data (e.g., comprising one or more unique patient identifiers) from a mobile device application instantiated on a mobile device (e.g., as shown in step 3070.

In some cases, a method 4000 can comprise receiving patient identifier data (e.g., comprising one or more UPIs) at a front-end medical imaging workflow application (FEMIWA), which may be instantiated on or serve as a virtual server (e.g., a cloud-based server 208), from a module of the mobile device application either after displaying patient identifier data on a mobile device display or after acquiring the patient identifier data (e.g., using a scanning module of the mobile device application, as described herein), for instance, as shown in step 4060 of FIG. 4. In some cases, a method 4000 can comprise transmitting all or a portion of the patient identifier data from the FEMIWA to an interface application (IA), which may be instantiated on a physical or virtual server 214 (e.g., as shown in step 4062 of FIG. 4). A module of an IA (e.g., a back-end data quality module of the IA) can be configured to receive the patient identifier data from the FEMIWA (e.g., as shown in step 4070).

As shown in FIG. 3 and FIG. 4, respectively, methods 3000 and 4000 can comprise creating an imaging session record (e.g., at an imaging session module of the IA) based on the patient identifier data (e.g., which may comprise one or more unique patient identifiers (UPIs)), as described herein and, for example, as shown in steps 3080 and 4080. In some cases, methods 3000 and 4000 can comprise receiving medical diagnostic data (e.g., comprising one or more medical images, videos, or multiframes) at a module of the IA (e.g., at an imaging session module of the IA), for example, as shown in steps 3090 and 4090. In some cases, a method 3000 or 4000 can comprise creating a medical imaging record based at least in part on all or a portion of the patient identifier data (e.g., one or more of the unique patient identifiers) and all or a portion of the medical diagnostic data (e.g., one or more medical images, videos, or multiframes) received from the medical imaging system, for example, as shown in step 3100 and step 4100. In some cases, a platform, system or method (e.g., method 3000 or 4000) described herein can comprise creating a medical imaging record based at least in part on all or a portion of the patient identifier data and all or a portion of a set of medical diagnostic data (e.g., one or more medical images, videos, or multiframes) present on the virtual or physical server 214 (e.g., stored on the server 214 or having previously been received from a medical imaging system, an EMR system, or another source, for example, via a wired or wireless network connection or telecommunications network connection). In some cases, a mobile device can be used to create the medical diagnostic data (e.g., wherein the mobile device comprises an ultrasound scanner) and, optionally, to create a medical imaging record based at least in part on all or a portion of the patient identifier data and all or a portion of the medical diagnostic data. A method 3000 or 4000 can comprise persisting the medical imaging record to an electronic medical records system (EMR system) (e.g., via an EMR module of the IA), for example as shown in step 3110 and step 4110.

Optionally, a method 3000 or 4000 can comprise transmitting, by the IA (e.g., by an EMR module of the IA), a patient record query (e.g., comprising one or more patient identifiers) to an electronic medical records system (EMR system), for example, after receiving the medical diagnostic data at the IA (e.g., as shown in step 3092 and 4092). Optionally, a method 3000 or 4000 can comprise receiving, by the IA (e.g., by an EMR module of the IA), patient record data (e.g., comprising one or more electronic medical records (EMRs) corresponding to the one or more patient identifiers transmitted to the EMR system via the EMR query) from the EMR system, for example, as shown in step 3094 and 4094 (e.g., prior to creation of the medical imaging record at the IA, which may be based in part on the one or more EMRs received by the EMR module).

Figure 5:
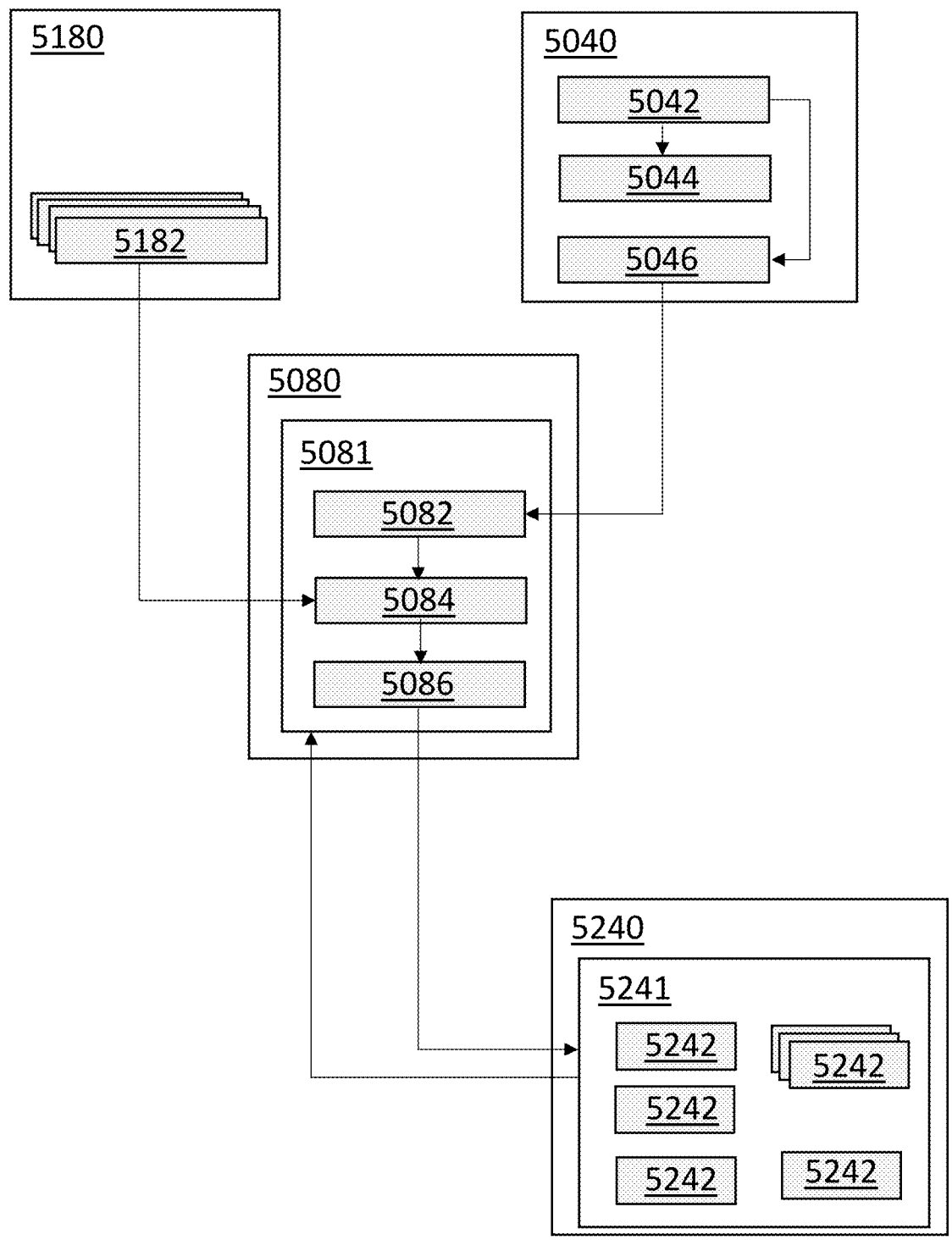
FIG. 5 shows an example of an architecture diagram, in accordance with embodiments; in this case, an architecture diagram including a healthcare provider application, a medical imaging device, a server, and a medical record database.

FIG. 5 shows a schematic representation of devices, platforms, and systems that can be useful in acquisition of medical diagnostic data, acquisition of patient identifier data, creation or modification of patient medical records, and/or upgrading existing medical equipment, such as medical imaging systems, e.g., as described herein. In some cases, a mobile device application 5040 (e.g., instantiated on a mobile device) can comprise a scanning module 5042, an accessibility module 5044, and/or a data quality module 5046 (e.g., a front-end data quality module). In some cases, a scanning module 5042 can be configured to acquire patient identifier data (e.g., comprising one or more patient identifiers), for instance, by interfacing with and/or operating a scanner or camera of the mobile device. In some cases, the scanning module 5042 can be configured to transmit all or a portion of the patient identifier data to an accessibility module 5044 of the mobile device application 5040. An accessibility module 5044 of the mobile device application 5040 can be configured to display (and optionally adjust the format or presentation of) all or a portion of the patient identifier data to a user (e.g., healthcare provider) to improve accessibility (e.g., legibility) of the patient identifier data to the user. In some cases, a scanning module 5042 of a mobile device application 5040 can be configured to transmit all or a portion of acquired patient identifier data to a data quality module 5046 of the mobile device application 5040. In some cases, a data quality module 5046 of a mobile device application 5040 can be configured to transmit all or a portion of the acquired patient identifier data to a physical or virtual server 5080 (e.g., to a data quality module 5082 of an interface application 5081 instantiated on the physical or virtual server 5080). In some cases, an interface application 5081 (e.g., instantiated on a physical or virtual server 5080) can comprise a data quality module 5082 (e.g., a back-end data quality module), an imaging session module 5084, and/or an EMR module 5086. In some cases, a data quality module 5082 of an interface application 5081 can be configured to transmit all or a portion of the patient identifier data to an imaging session module 5084 of the interface application 5081. In some cases, an imaging session module 5084 of an interface application 5081 can be configured to receive medical diagnostic data (e.g., comprising one or more medical images, videos, or multiframes 5182) from a medical imaging system 5180 (e.g., an existing medical imaging system). In some cases, an imaging session module 5084 of an interface application 5081 can be configured to create a medical imaging record (e.g., based on all or a portion of the patient identifier data and all or a portion of the medical diagnostic data). In some cases, an imaging session module 5084 can be configured to transmit the medical imaging record to an electronic medical record module 5086 (EMR module) of the interface application

5080. In some cases, the EMR module is configured to persist the medical imaging record to a data store 5241 of an electronic medical record system 5240 (EMR system). In some cases, an EMR module 5086 is configured to receive one or more electronic medical records 5242 (EMRs) from an EMR system 5240, for example, in response to an EMR query, which may be transmitted to the EMR system 5240 by the EMR module 5086, for instance as a result of an EMR query initiation signal transmitted from a data quality module 5046 of the mobile device application 5040 to the interface application 5081. In some cases, all or a portion of the information comprising the EMR can be modified by (e.g., by adding all or a portion of the medical imaging record) or incorporated into the medical imaging record. In some cases, one or more (e.g., modified or unmodified EMRs) can be transmitted from the EMR module 5086 to the EMR system 5240 or a portion thereof. In some cases, all or a portion of the information comprising one or more EMRs 5242 received by a module of the interface application 5080 can be transmitted to the mobile device application 5040, for instance, for display on a screen of the mobile device (e.g., by the accessibility module 5044).

Healthcare Provider Applications

Platforms, systems, and methods disclosed herein can comprise a mobile device application 5040 (e.g., a healthcare provider application). As described herein, mobile device application can aid in the acquisition of patient identifier(s) (e.g., patient identifier data 202) and can facilitate the creation of combined medical data files (e.g., medical imaging records), which can comprise clinical diagnostic data (e.g., medical image data) and one or more patient identifier(s). The flexibility and ease of use afforded by mobile device applications described herein can increase quality of clinical diagnostic data, for instance, when utilized in outpatient or critical care situations (e.g., emergency department care), when opportunities for patient identifier collection may be limited and/or stressful and continuity of patient identifiers and diagnostic data acquisition can be vulnerable.

A mobile device application (e.g., healthcare provider application) can be instantiated on a mobile device used by a healthcare provider, such as a clinician provider (e.g., a doctor, nurse practitioner, physician's assistant, or clinical nurse specialist) or a medical technician (e.g., a paramedic, an ultrasound technician, an electroencephalograph technician, or a radiology technician, such as a X-ray technician). For instance, a mobile device application may be run on a healthcare provider or technician's personal phone or a phone owned and/or operated by a medical facility and used by a department or individual responsible for patient care or data acquisition. In some cases, a mobile device application described herein can be implemented as a native mobile application. For example, a mobile device application can be coded into an operating system of the mobile device, which can improve speed and reliability of the application's function on the mobile device. In some cases, a mobile device application can be implemented as a mobile web application. In some cases, a mobile device application can be downloaded to the mobile phone (e.g., via a network). Downloadable mobile device applications described herein can be used to upgrade an existing mobile device not equipped with the mobile device application as a native mobile application. In some cases, the portability and accessibility of a mobile device can reduce the likelihood of data quality loss, as a provider or technician may be more apt to record patient identifiers immediately, e.g., as compared to the use of a desktop or laptop computer terminal or a handwritten log system, which may require a provider or technician to log in separately and/or pause care of the patient to input patient identifier data.

A mobile device 204 on which a mobile device application 5040 (e.g., healthcare provider application) described herein is instantiated can comprise an imaging device. For example, an imaging device of a mobile device can comprise a camera, which can, for example, be used to acquire patient identifier information (e.g., optical image data that may comprise a unique patient identifier). A mobile device application can be configured to receive data from an imaging device of a mobile device on which the mobile device application is instantiated. In some cases, a mobile device application described herein can be configured to control data (e.g., patient identifier) acquisition, for instance, by interfacing with and/or operating an imaging device of the mobile device. In some cases, a mobile device application 5040 (e.g., healthcare provider application) can comprise a scanning module 5042. A scanning module of a mobile device application can be configured to acquire a patient identifier associated with a patient. For instance, a scanning module of a mobile device application can be configured to receive image data comprising a barcode, a numeric or alphanumeric code (e.g., unique patient identifier, hospital patient identification (ID) number, patient name, patient address, social security number, patient gender), or other patient identifier data (e.g., a fingerprint scan or retinal scan). A scanning module 5042 of a mobile device application 5040 can be configured to transmit patient identifier data (e.g., one or more patient identifiers) to an accessibility module 5044 of the mobile device application, e.g., for display of the patient identifier data on a screen of the mobile device. In some cases, a scanning module of a mobile device application can be configured to convert data received from an imaging device of a mobile device from a first format (e.g., an image format) to a second format (e.g., a text format), for example, to increase compatibility of the patient identifier information received from the imaging device of the mobile device with other data from the patient's medical imaging record or electronic medical record (EMR) and/or to decrease the amount of time required of an individual (e.g., a provider, a technician, or other staff member) to convert image data to data compatible with a medical record or otherwise incorporate the patient identifier(s) captured in the image data into the patient's diagnostic imaging data and/or medical imaging record. A scanning module 5042 can be configured to transmit patient identifier data (e.g., one or more patient identifiers) to a data quality module 5046 of the mobile device application, e.g., for subsequent transmission to a server 5080 of a platform, system, or method described herein.

In some cases, a scanning module can interface with a camera of the mobile device and the display of the mobile device, for example, to assist in the acquisition of patient identifier data. In some cases, optical data from the camera can be provided from the camera to the display in a live feed, e.g., to provide a user with a visual reference for adjusting focus, distance, orientation, framing, and/or lighting during acquisition of patient identifier data. Such visual reference can reduce the likelihood that acquisition of patient identifier information would need to be reattempted (e.g., due to poor acquisition of image data with the camera rendering the patient identifier data incomplete or indecipherable). In some cases, a guidance reticle can be displayed to aid in positioning and focusing of the camera (e.g., relative to a patient identifier target comprising patient identifier data) during patient identifier data acquisition. In some cases, a guidance reticle can comprise a shape and positioning on the screen that indicates optimal positioning of the camera relative to the patient identifier target for patient identifier data acquisition. In some cases, the guidance reticle shape can be round (e.g., circular, for example, to capture retinal or iris pattern data), rectangular (e.g., to capture linear barcode, numeric, or alphanumeric data), or square (e.g., to capture 2D barcode data).

In some cases, a scanning module can be configured to receive all or a portion of a set of patient identifier(s) via direct user input. For instance, a scanning module can be configured to receive numeric or alphanumeric patient identifier data via a keypad displayed on the mobile device's screen. In some cases, a scanning module can be configured to receive drawn patient identifier data (e.g., data handwritten on the screen of the mobile device using a finger or stylus compatible with the mobile device).

In some cases, a mobile device application 5040 (e.g., a healthcare provider application) can comprise an accessibility module 5044. An accessibility module can be configured to provide a healthcare provider with an accessibility display via a screen of the mobile device. An accessibility module can be configured to receive patient identifier data (e.g., one or more unique patient identifiers) from a scanning module 5042 of the mobile device application 5040. One or more patient identifiers (e.g., which have been acquired via an imaging device of the mobile device and/or which has been input directly into the mobile device via typed or drawn input from a user) can be displayed to a user (e.g., a healthcare provider) by the accessibility module (e.g., via the accessibility display). In some cases, presentation of patient identifier data (e.g., received by the mobile device application via a scanning module and/or an accessibility module) to a user can allow the user to verify accuracy and/or completeness of patient identifier data at the time of patient identifier data acquisition. In some cases, this can improve data quality by alerting the user to an error in patient identifier data while the opportunity for patient identifier acquisition is still present. For example, displaying patient identifier data to the user via an accessibility module can render obvious any typographical errors and/or data reading or conversion errors (e.g., resulting from blurry, poorly framed, or poorly lit images).

Furthermore, an accessibility module 5044 can be configured to improve the ease of understanding information displayed (e.g., by the mobile device via a healthcare provider accessibility interface) by the mobile device application (e.g., healthcare provider application), which can include one or more patient identifiers and/or information from a patient's medical imaging record and/or a patient's medical record. In some cases, an accessibility module can be configured to make text more readable, for example by increasing the size of the text displayed on a screen of the mobile device, by modifying color and/or intensity of portions of the display (e.g., adjusting or reversing contrast of the display to improve readability and decrease strain on the eyes and/or adjusting colors of the display, for example, to account for color blindness in a user), by converting text to speech (e.g., to reduce the need for a user to divert their attention away from a patient and/or to account for decreased visual acuity in a user), and/or by translating verbal commands provided by the user into executable commands capable of controlling one or more functions of the mobile device application (e.g., to reduce the need for a user to divert their attention away from a patient). In some cases, a healthcare accessibility interface can comprise an audio presentation of patient identifier data (e.g., created via text-to-speech or image-to-speech computer protocols). In some cases, a healthcare accessibility interface can comprise an enlarged, high contrast presentation of patient identifier data (e.g., displayed on a screen of the mobile device).

In some cases, numeric, alphanumeric, and/or drawn patient identifier data can be received by the mobile device application via an accessibility module of the mobile device application. In some cases, a scanning module of a mobile device application can interface with a scanning module of the mobile device application. In some cases, numeric, alphanumeric, and/or drawn patient identifier data (e.g., received by a scanning module and/or an accessibility module of the mobile device application) can be incorporated into or associated with patient identifier data captured by an imaging device of the mobile device (e.g., as image data) by the mobile device application. In some cases, a mobile device application can be configured to transmit patient identifier data received via a scanning module and/or an accessibility module and image data received via a scanning module directly or indirectly to a server (214, 5080) of a platform or system described herein.

A mobile device application 5040 (e.g., healthcare provider application) can comprise a data quality module (e.g., a front-end data quality module 5046). A data quality module of a mobile device application 5040 (e.g., a front-end data quality module 5042) can be configured to receive patient identifier data (e.g., one or more patient identifiers) from a scanning module of the mobile device application, e.g., for subsequent transmission to a server 5080 of a platform, system, or method described herein. In some cases, a data quality module (e.g., a front-end data quality module 5042) of a mobile device application 5040 can be configured to convert data received from an imaging device of a mobile device (e.g., via a scanning module) from a first format (e.g., an image format) to a second format (e.g., a text format), for example, to increase compatibility of the patient identifier information received from the imaging device of the mobile device with other data from the patient's medical imaging record or electronic medical record (EMR) and/or to decrease the amount of time required of an individual (e.g., a provider, a technician, or other staff member) to convert image data to data compatible with a medical record or otherwise incorporate the patient identifier(s) captured in the image data into the patient's diagnostic imaging data and/or medical imaging record. A data quality module of a mobile device application can be configured to transmit data, which can comprise data acquired or received by the mobile device application (e.g., patient identifier data acquired via manual input by a user and/or via image data capture by an imaging device of the mobile device) over a network, for example, to an interface application 5081 of a server 5080. In some cases, a data quality module (e.g., front-end data quality module) can be configured to transmit data wirelessly over a network. In some cases, a data quality module of a mobile device application can be configured to transmit data to one or more servers (e.g., comprising one or more physical servers and/or one or more virtual servers, such as cloud-based applications). In some cases, a data quality module of a mobile device application can be configured to transmit data (e.g., to one or more servers (208, 214, 5080), which may include one or more remote servers) via a telecommunications network. In some cases, a data quality module of a mobile device application can be configured to transmit data (e.g., to one or more servers (208, 214, 5080), which may include one or more local servers), via short-range wireless communication (e.g., via a wireless local area network (WLAN), such as a Wi-Fi network, via a personal area network (PAN), such as Bluetooth or ZigBee™, or via an ultra wideband (UWB) system). In some cases, a data quality module of a mobile device application instantiated on a mobile device 204 can be configured to transmit data (e.g., comprising patient identifier data 202) to a first (e.g., virtual) server 208 (e.g., as shown in path 206 of FIG. 2) before being transmitted by the first (e.g., virtual) server 208 to a second (e.g., physical) server 214 (e.g., as shown in path 210 of FIG. 2). In some cases, a data quality module of a mobile device application instantiated on a mobile device 204 can be configured to transmit data (e.g., comprising patient identifier data 202) to a (e.g., physical) destination server 214 directly (e.g., without first being transmitted to a first (e.g., virtual) server, for example, as schematically illustrated in FIG. 2). A data quality module (e.g., a front-end data quality module 5046) of a mobile device application 5040 can be configured to transmit data (e.g., comprising patient identifier data, such as one or more unique patient identifiers) directly or indirectly to a data quality module (e.g., a back-end data quality module 5082) of an interface application 5081 of a server 5080, for instance as shown in FIG. 2 and FIG. 5.

In some cases, a mobile device application (e.g., healthcare provider application) can comprise a login module (e.g., a healthcare provider sign-in module). A login module of a mobile device application can be configured to challenge a user with a login prompt (e.g., wherein the login prompt is displayed on a screen of the mobile device), for example, to verify the identity of the user (e.g., the healthcare provider). In some cases, the login module can validate user input into the login prompt against a list of access credentials stored on the mobile device. In some cases, the login module can transmit information input by the user into the login prompt to a remote server or database (e.g., via a wireless network connection). In some cases, a login module can initiate a user interface and display the user interface on the screen of the mobile device, for instance upon successful validation of user login information or, for example in embodiments not requiring a user to input valid login information, upon initial use of the mobile device. In some cases, a user interface of a mobile device application can comprise options for a user to initiate a scan (e.g., operation of a camera of the mobile device, for example, to acquire patient identifier data). In some cases, a user interface of a mobile device application can comprise an option for sending patient identifier data (e.g., comprising one or more unique patient identifiers) to an interface application, for sending instructions to the interface application to combine a set of patient identifier data with a set of medical images, videos, or multiframes created by a medical imaging system (e.g., to create a medical imaging record), for sending an electronic medical record (EMR) query (e.g., which may produce and transmit an EMR query initiation signal, as described herein), for accessing patient information comprised within an EMR, and/or for persisting a medical imaging record to a data store of an electronic medical record system (EMR system) (e.g., in embodiments wherein persisting one or more medical imaging records to the EMR system is not automatically performed by an interface application).

Interface Applications

Platforms, systems, and methods disclosed herein can comprise an interface application 5081. As described herein, interface applications can aid in the combination of patient identifier(s) (e.g., patient identifier data 202) with clinical diagnostic data (e.g., medical image data) in the form of combined medical data files (e.g., medical imaging records). An interface application, which can be instantiated on a local server (214, 5080) or a remote server (214, 5080) can comprise a data quality module 5082 (e.g., a back-end data quality module) configured to receive patient identifier data (e.g., comprising one or more patient identifiers), for example, via a wired or wireless connection with a mobile device 204 comprising a mobile device application 5040. In some cases, an interface application (e.g., a data quality module 5082 of an interface application) can be configured to receive patient identifier data (e.g., comprising one or more unique patient identifiers) from a data quality module 5046 (e.g., a front-end data quality module) of a mobile device application 5040. In some cases, a data quality module 5046 of an interface application 5081 can be configured to transmit patient identifier data (e.g., patient identifier data received from a mobile device application 5040, which may comprise one or more patient identifiers) to an imaging session module 5084 of the interface application 5081.

An interface application 5081 can comprise an imaging session module 5084, which can be configured to receive clinical diagnostic data (e.g., comprising one or more medical images, videos, or multiframes 5182, for example, acquired using a medical imaging system 218, 5180), e.g., from a medical imaging system (218, 5180), for example, via a wired or wireless connection. An imaging session module 5084 of an interface application 5081 can be configured to receive patient identifier data (e.g., comprising one or more patient identifiers) from a data quality module 5082 of the interface application 5081. In some cases, an imaging session module 5084 of an interface module can be configured to create an imaging session record, which may comprise patient identifier data (e.g., received from a data quality module 5082 of the interface application 5081) and clinical diagnostic data 5182 (e.g., received from a medical imaging system 5180. In some cases, an imaging session module 5084 of an interface application 5080 can be configured to create an imaging session record using patient identifier data (e.g., one or more unique patient identifiers) received from a mobile device application (e.g., via a data quality module 5082 of the interface application 5081). In some cases, an imaging session module 5084 of an interface application 5081 can be configured to create an imaging session record using clinical diagnostic data 5182 (e.g., comprising one or more medical images, videos, or multiframes). In some cases, an imaging session module 5084 of an interface application 5081 can be configured to create an imaging session record (e.g., using patient identifier data) prior to receiving at least a portion of the clinical diagnostic data. In some cases, such a configuration can decrease data loss by creating a destination for subsequently produced clinical diagnostic data (e.g., comprising at least one medical image) that is associated with a unique patient identifier, which can keep clinical diagnostic data together and can render the data easily accessible and transferrable. In some cases, an imaging session module of an interface application can be configured to create an imaging session record (e.g., using patient identifier data and/or clinical diagnostic data) after receiving at least a portion of the clinical diagnostic data. As such, an interface application can be flexible with respect to adding a unique patient identifier to an existing set of clinical diagnostic data (e.g., in situations wherein no opportunity to obtain unique patient identifiers occurred before the creation of the clinical diagnostic data or wherein patient identifier data received from a mobile device application was corrupted or indecipherable) or adding clinical diagnostic data to a server-based destination created using patient identifier information. An imaging session module can be configured to create a medical record, for example, wherein the medical imaging record is created based at least in part on the patient identifier data (e.g., comprising a unique patient identifier) and at least a portion of a set of clinical diagnostic data (e.g., comprising at least one medical image, for example, wherein the at least one medical image is received by the interface application from a medical imaging system).

An interface application 5081 can be configured to receive data from and/or transmit data to a mobile device application 5040 (e.g., a healthcare provider application). In some cases, patient identifier data (e.g., comprising a unique patient identifier) can be received by an interface application 5081 (e.g., by a back-end data quality module 5082 of the interface application 5081) directly from a mobile device application 5040 (e.g., from a front-end data quality module 5046 of a mobile device application 5040 instantiated on the mobile device), for example, via a wired or wireless network connection. In some cases, patient identifier data can be received by an interface application (e.g., by a back-end data quality module 5082 of the interface application 5081) indirectly from a mobile device. For example, patient identifier data can be received by an interface application (e.g., by a back-end data quality module 5082 of the interface application 5081) from a physical or virtual (e.g., cloud-based) server 208, which can be configured to receive the patient identifier data from the mobile device application 5040 (e.g., a data quality module 5046 of a mobile device application 5040) and transmit the patient identifier data to the interface application (e.g., which may be instantiated on a physical server 214 or virtual server), e.g., via a wired or wireless network connection in some embodiments.

An interface application can comprise an electronic medical record module 5086 (EMR module). An EMR module 5086 of an interface application 5081 can be configured to receive a medical imaging record (e.g., created at an imaging session module 5084 of the interface application 5081) from an imaging session module 5084 of the interface application 5081. An EMR module 5086 of an interface application 5081 can be configured to persist a medical imaging record (e.g., created using an imaging session module of the interface application) to an electronic medical record for a patient at a data store of an electronic medical records system (EMR system), which can comprise a plurality of patient electronic medical records (EMRs), e.g., via a wired or wireless network connection. In some cases, an interface application 5081 (e.g., an EMR module 5086 of the interface application) can be configured to retrieve patient information from an EMR system 5240 (e.g., a data store 5241 of the EMR system 5240) by transmitting patient identifier data (e.g., comprising a unique patient identifier) to the EMR system. For example, an EMR module 5086 can transmit an EMR query (e.g., comprising patient identifier data, which may have been acquired by a mobile device application 5040 of the platform, system, or method) to an EMR system 5240, as described herein. In some cases, an interface application 5081 (e.g., an EMR module 5086 of an interface application 5081) can be configured to receive one or more EMRs 5242 (e.g., corresponding to one or more patient identifiers received from the mobile device application) from an EMR system 5240 (e.g., in response to an EMR query transmitted by the EMR module 5086 to the EMR system 5240 or portion thereof). In some cases, a data store 5241 of an EMR system 5240 can be a database server. In some cases, a data store 5241 of an EMR system 5240 can be a cloud data store.

In some cases, an interface application 5080 can be configured to transmit a medical imaging record (e.g., comprising one or more patient identifiers and one or more medical images, videos, or multiframes) to a communication server. For example, a user may wish to transmit a copy of the medical imaging record to an email address or to a database other than an EMR system (e.g., a file management system of an entity operating a medical facility). Accordingly, a medical imaging record can be transmitted to a healthcare provider (e.g., the user or a provider identified by the user for referral of the medical case or contents of the medical imaging record), which can allow for subsequent review of the medical imaging record separately from use of the mobile device application.

Patient Identifiers

Platforms, systems, and methods disclosed herein can comprise one or more patient identifier(s), acquisition of one or more patient identifier(s), and/or means for acquiring one or more patient identifier(s). A patient identifier can be a unique patient identifier. A patient identifier (e.g., a unique patient identifier) can comprise a text string, a number, a biometric feature of a patient (e.g., a fingerprint, palm print, iris pattern, face recognition pattern, or retinal pattern), a linear barcode, a 2D barcode, or a combination of thereof. In some cases, a patient identifier comprises one or more of: a unique patient identifier, a hospital patient identification (ID) number, a patient name, a patient address, a government-issued identification number (e.g., a social security number, a passport number, a driver's license number, a military service number (e.g., a U.S. Department of Defense ID number), or information from a military dog tag), or a patient gender. In some cases, a unique patient identifier allows identification of a specific individual.

Medical Imaging Systems

Platforms, systems, and methods disclosed herein can comprise a medical imaging system. A medical imaging system can be an existing medical imaging system, which may be in need of upgrading (e.g., a retrofit upgrade). In some cases, a medical facility may own and/or operate a medical imaging system (e.g., an "existing medical imaging system") that lacks a given functionality. In some cases, a medical imaging system owned and/or operated by a medical facility (e.g., an "existing medical imaging system") may lack one or more functionalities that render the system vulnerable to or prone to decreased data quality (e.g., data loss). For instance, an existing medical imaging may lack means for collecting patient identifier data (e.g., one or more patient identifiers) and/or means for creating a combined record comprising a medical image (e.g., produced by the existing medical imaging system) and one or more patient identifiers. In some cases, such shortcomings of medical imaging systems (e.g., "existing medical imaging systems") result in a need for manual processing of medical diagnostic data (e.g., comprising one or more medical images, videos, or multiframes) to ensure the medical diagnostic data is identified with the proper patient identification data or the use of multiple, potentially incompatible and/or asynchronously updated third-party data processing software packages, which may lead to decreased data loss (e.g., via improper or incomplete labeling of medical diagnostic data). As described herein, medical imaging system(s) (e.g., "existing medical imaging systems") lacking one or more such functionalities (e.g., in need of upgrading) can be upgraded using platforms, systems, methods described herein (or portions thereof) to add one or more functionalities not present in the medical imaging system(s), thereby increasing data quality in conjunction with the use of the medical imaging system(s). In some cases, a medical imaging system (e.g., an existing medical imaging system in need of upgrading) may lack means for acquiring patient identifier (e.g., from a patient identifier target, such as a bracelet, sheet of paper, or other media comprising a barcode or written text comprising patient identifier information, or a source of biometric information, such as an eye, finger, or palm). Accordingly, a medical imaging system described herein (e.g., an existing medical imaging system in need of upgrading) may not have access to patient identifier data (e.g., to one or more unique patient identifiers, for example, of a patient for which the medical imaging system is used to generate one or more medical images, video, or multiframes). In some cases, a medical imaging system (e.g., an existing medical imaging system in need of upgrading) is connected to a local computer network and/or a telecommunication network (e.g., via a wired or wireless connection). In some cases, a medical imaging system (e.g., an existing medical imaging system in need of upgrading) is not connected to a local computer network and/or telecommunication network. In some cases, a medical imaging system (e.g., an existing medical imaging system in need of upgrading) may not be configured to and/or able to communicate directly with a mobile device and/or a mobile device application (e.g., healthcare provider application) described herein. In some cases, platforms, systems, and methods described herein can be configured to establish an upgraded medical imaging system (e.g., comprising an existing medical imaging system, which may be in need of upgrading). In some cases, platforms, systems, and methods described herein can be configured to establish an upgraded medical imaging system (e.g., comprising the existing medical imaging system) without modifying the existing medical imaging system. A medical imaging can comprise an ultrasound device, an x-ray radiography device, a magnetic resonance imaging (MRI) device, an endoscopy device, a thermography device, a photography device, an X-ray computed tomography (CT) device, a positron emission tomography (PET) device, a single-photon emission computed tomography (SPECT) device, a photoacoustic imaging device, or a combination thereof. A medical imaging system can comprise an ultrasound system or portion thereof (e.g., an ultrasound device, such as a handheld ultrasound scanner or portable ultrasound machine).

In many cases, a medical imaging system described herein can produce one or more medical image (e.g., one or more diagnostic medical images, videos, or multiframes), for example, during examination and/or treatment of a patient. In some cases, a medical imaging system can produce at least one medical image during examination and/or treatment of a patient. In some cases, a medical imaging system can produce a plurality of medical images, videos, or multiframes during examination and/or treatment of a patient. In some cases, a medical imaging system can be configured to transmit one or more medical images, videos, or multiframes to a server (e.g., a server 214, 5080 comprising an interface application as described herein), e.g., via a wired or wireless connection, as described herein. In some cases, a medical imaging system can be configured to store one or more medical images, videos, or multiframes to a non-transitory memory of the medical imaging system and/or to a non-transitory memory of a computer connected to the medical imaging system (e.g., for subsequent upload to a server described herein). In some cases, a medical imaging system employs Digital Imaging and Communications in Medicine (DICOM) formatting in display, storage, and/or transmission of medical image(s). For example, a medical imaging system can be DICOM-enabled.

Electronic Medical Record Systems

Platforms, systems, and methods disclosed herein can comprise an electronic medical record system. An electronic medical record system 224, 5240 (EMR system) can comprise a means for electronic storage of patient electronic medical record files 5242 (EMRs). In some cases, an application described herein (e.g., an EMR module of an interface application) can transmit an EMR query to an EMR system requesting retrieval of one or more patient electronic medical record files 5242 (EMRs), e.g., via a wired or wireless network connection. In some cases, an EMR query can be initiated by a mobile device application (e.g., a healthcare provider application), for example, via an EMR query initiation signal generated by input from a user and/or after provision of one or more patient identifiers (e.g., one or more unique patient identifiers) by the mobile device application. In some cases, a mobile device application can be configured to automatically generate an EMR query initiation signal after acquisition of one or more patient identifiers (e.g., via user input and/or acquisition by an image device of a mobile device). In some cases, EMR query initiation signal can comprise one or more patient identifiers (e.g., as determined by user input and/or acquisition by an image device of a mobile device). An EMR query initiation signal can be transmitted directly from a mobile device application (e.g., a front-end data quality module of the mobile device application) to an interface application (e.g., to a back-end data quality module of an interface application), for example, via a wired or wireless network connection. In some cases, an EMR query initiation signal can be transmitted indirectly from a mobile device application (e.g., a front-end data quality module of the mobile device application) to an interface application (e.g., to a back-end data quality module of an interface application), for example, via a wired or wireless network connection. For example, an EMR query initiation signal can be transmitted from a mobile device application (e.g., a front-end data quality module of the mobile device application) to a first network node (e.g., a physical or virtual (e.g., cloud-based) server) in some embodiments. In some cases, the EMR query initiation signal received by the first network node (e.g., a physical or virtual server) can then be transmitted by the first network node 208 to a second network node 214, 5080, which can comprise an interface application and may be configured to receive the EMR query initiation signal at a back-end data quality module of the interface application. An EMR query initiation signal can optionally be modified by an interface application of a network node 214, 5080 (e.g., which can comprise a physical or virtual server) from a first format to a second format, for instance, if the EMR system requires that EMR queries be in a format different than that of the EMR query initiation signal. An interface application can be configured to transmit an EMR query, which may comprise a modified or unmodified EMR query initiation signal, to an EMR system, e.g., via a wired or wireless network connection. The EMR query can comprise one or more patient identifiers and can include a request for the EMR system to retrieve and transmit one or more EMRs stored at a data store of the EMR system that correspond to the one or more patient identifiers. In some cases, a data store of an EMR system can comprise a database server. In some cases, a data store of an EMR system can comprise a cloud data store. An interface application can be configured to receive the one or more EMRs transmitted by the EMR system to the network node 214, 5080 based on the EMR query.

A non-exhaustive list of current EMR services that may comprise a portion of an EMR system of the platforms, systems, and methods described herein include: TherapyNotes™, Sevocity®, Care360®, Practice Fusion, Cerner, Optum Physician, EpicCare, Office Ally EHR 24/7, InteGreat EHR, Kareo Clinical, TouchWorks HER, CampDoc, Centricity EMR, NextGen Healthcare, PointClickCare, Amazing Charts, Praxis, InSync EMR, MDVision PM EMR, Nextech EMR, AthenaHealth®, AdvancedMD, Clinicient INSIGHT, PrognoClS, MicroMD, AllegianceMD, ABELMed, ReLi Med Solutions, iClinic Systems, or OpenEMR.

Data Quality

Data quality in medical settings, which can depend on maintaining accurate and complete data records, is an area of major concern for healthcare providers and organizations responsible for the administration of medical facilities. In many cases, existing medical equipment (e.g., medical imaging systems) operated and owned by such providers and organizations lack functionalities that would improve data quality, such as means for capturing patient identifier data in a clinical setting (e.g., as opposed to collection of patient identifier data in an administrative setting, which may occur at a different time or place than the usage of the medical equipment and may lead to errors or omissions when patient identifiers are subsequently added to medical diagnostic data, such as medical imaging data). In many cases, patient identifiers, which may be important for incorporating newly produced medical diagnostic data into a patient's existing electronic medical record (EMR), are added to medical image files manually. This can lead to difficulty finding or identifying newly produced medical diagnostic data within an organization's file management system, which can in turn lead to loss of data (e.g., which may require that diagnostic imaging be performed again). In some cases, medical equipment (e.g., existing medical imaging systems) lacking such functionalities important for maintaining data quality may increase the risk of a misdiagnosis or erroneous treatment (e.g., as a result of incorrect patient identifier information being associated with a given data point or data set).

Modernization of existing medical equipment is extremely expensive, as manufacturers infrequently market upgrades for existing systems, choosing instead to offer newer models of complete systems for sale. Thus, providers and organizations owning and operating medical imaging systems, which may lack various functionalities useful in maintaining data quality and which tend to require complete replacement, often go years or even decades without acquiring new equipment having such functionalities. When such systems are acquired, usually at great cost, decommissioning of outdated existing systems and installation and training for newly purchased systems can be disruptive and can be wasteful if the existing equipment is disused but still operational (e.g., because of a lack of functionality, such as a lack of network connectivity or of means of acquiring and integrating patient identifiers with produced medical diagnostic data).

Platforms, systems, and methods disclosed herein offer an alternative paradigm in which existing medical equipment (e.g., existing medical imaging systems) can be provided with functionalities important for maintaining or increasing data quality. In many cases, platforms, systems, and methods disclosed herein can confer such benefits on existing medical imaging systems without modification of the existing medical imaging systems. Furthermore, the platforms, systems, and method disclosed herein can be subsequently upgraded themselves without the need to upgrade the medical equipment (e.g., medical imaging systems) benefitting from the added functionalities they provide.

Timestamps

In some cases, data quality in a platform, system, or method described herein can be improved by incorporating a timestamp (e.g., comprising a date, a time, or a combination thereof) into data recorded and/or transmitted in the course of utilizing the platform, system, or method. In some cases, a timestamp can be incorporated into a request, a query, medical diagnostic data (e.g., comprising one or more images), a record (e.g., an imaging session record, a medical imaging record, or a patient electronic medical record), and/or an identifier (e.g., a unique patient identifier). In some cases, one or more components comprising a platform or system described herein or utilized in the practice of a method described herein may utilize data comprising a timestamp, for example, to index or log the date and/or time of creation or modification of a portion of data (e.g., an image, record, request, or query) and/or to queue an operation (e.g., comprising transmission, receipt, or execution of a request or query) among other one or more same, similar, or different operations of the platform, system, or method. In some cases, a timestamp created or modified by a first component comprising or interacting with a platform or system described herein or utilized in the practice of a method described herein may not correspond to a timestamp created or modified by a second component which comprises or interacts with the platform or system or which is utilized in the practice of the method, for example, as a result of a lack of synchronization of time measurement systems internal to or used by the first and second components and/or as a result of differences in format of timestamp data between the first and second components (e.g., arising from differences in time zone, from differences in the format of the timestamp, such as the use of a 24-hour clock or 12-hour clock, or from differences in timestamp format convention, such as the order of month, day, year, and/or time). In some cases, such differences can adversely affect data quality, for example, by introducing uncertainty or errors in the use (e.g., function) of the platform, system, or method or in the use (e.g., interpretation) of data created, modified, or updated in the implementation of the platform, system, or method. In some embodiments, a platform, system, or method herein can comprise creating a timestamp or modifying an existing timestamp (e.g., a timestamp created by a device, module, or server described herein, or a timestamp created by an existing medical imaging system and, optionally, incorporated into a medical image created by the existing medical imaging system). In some cases, creating, incorporating, or modifying a timestamp can improve validation and/or accuracy of the transmission or receipt of data (e.g., comprising a query, request, medical diagnostic data, or record) and/or of the combination of a first and second portion of data (e.g., during creation or modification of an imaging session record, a medical imaging record, or a patient electronic medical record). In some cases, a first set of one or more timestamps incorporated into (e.g., added to) a first set of data (e.g., a query, request, medical diagnostic data, or record), for example by a healthcare provider application, an interface application, an existing medical imaging system, and/or an EMR system, can be compared with a second set of one or more timestamps incorporated into a second set of data and/or with a time measurement system of a device or system described herein (e.g., during transmission, receipt, or modification of the first and/or second set of data). For example, a timestamp of a portion of (e.g., DICOM-formatted) medical diagnostic image data

5182 (e.g., wherein the timestamp is created in the portion of medical diagnostic data by a medical imaging system) can be compared to a timestamp of an identifier (e.g., a timestamp incorporated into a unique patient identifier by a healthcare provider application) for use in creating or modifying a medical imaging record based on the medical diagnostic data 5182 and the identifier (e.g., by an interface application), for instance to ensure that the medical diagnostic data is being combined with the correct identifier, even if differences exist between the time or order that a server (e.g., used to create or modify the medical imaging record) receives the medical diagnostic data and/or identifier (e.g., amongst a plurality of identifiers and/or a plurality of portions of medical diagnostic data, may either or both comprise identifier(s) or data from different patients or different imaging sessions). In some cases, a timestamp can be modified (e.g., by a healthcare provider application, an interface application, an EMR system, and/or a virtual server 208), for example, to correct for a difference between a time measurement system and/or a timestamping function of a first component of a platform, system, or method described herein and a time measurement system and/or timestamping function of a second component of the platform, system, or method (e.g., a difference between the time measurement systems and/or timestamping functions is known to exist or is apparent or discernible from other available information, such as file name, file size, file format, and/or identifier(s) associated with the timestamped data), or to synchronize the timestamps created by such first and second components.

Accessibility

Platforms, systems, and methods disclosed herein can also improve the ease of use of existing medical equipment (e.g., existing medical imaging systems), which may not offer display and/or customization options that may be important for certain users or in certain settings. For example, existing medical equipment may lack portability, which can be important for providers, who are constantly moving from location to location in a medical facility and may use multiple different versions of a given type of medical equipment (e.g., different ultrasound imaging systems that may utilize different operating systems, file management systems, or accessibility options). In many cases, platforms, systems, and methods described herein can be easily adapted to interface with a plurality of disparate medical imaging systems and to consolidate the medical diagnostic data (e.g., comprising medical images and/or video and/or multi-frames) into a single medical record. Furthermore, platforms, systems, and methods disclosed herein may add functionality to existing systems that improves the ease of understanding information displayed to the user. For instance, platforms, systems, and methods described herein can be configured to make text more readable, for example by allowing a user to increase the size of the text displayed on a screen of the mobile device, by allowing modification of color and/or intensity of portions of the user interface (e.g., by adjusting or reversing contrast of the display to improve readability, which can decrease strain on the eyes and/or by adjusting colors of the display, for example, to account for color blindness in a user), by converting text to speech (e.g., to reduce the need for a user to divert their attention away from a patient and/or to account for decreased visual acuity in a user), and/or by translating verbal commands provided by the user into executable commands capable of controlling one or more functions of the mobile device application (e.g., to reduce the need for a user to divert their attention away from a patient.

Computing System

Platforms, systems, and methods disclosed herein can comprise one or more computing systems and/or the use thereof. Referring to FIG. 1, a block diagram is shown depicting an exemplary machine that includes a computer system 100 (e.g., a processing or computing system) within which a set of instructions can execute for causing a device to perform or execute any one or more of the aspects and/or methodologies for static code scheduling of the present disclosure. The components in FIG. 1 are examples only and do not limit the scope of use or functionality of any hardware, software, embedded logic component, or a combination of two or more such components implementing particular embodiments.

Computer system 100 may include one or more processors 101, a memory 103, and a storage 108 that communicate with each other, and with other components, via a bus 140. The bus 140 may also link a display 132, one or more input devices 133 (which may, for example, include a keypad, a keyboard, a mouse, a stylus, etc.), one or more output devices 134, one or more storage devices 135, and various tangible storage media 136. All of these elements may interface directly or via one or more interfaces or adaptors to the bus 140. For instance, the various tangible storage media 136 can interface with the bus 140 via storage medium interface 126. Computer system 100 may have any suitable physical form, including but not limited to one or more integrated circuits (ICs), printed circuit boards (PCBs), mobile handheld devices (such as mobile telephones (e.g., smartphones) or PDAs), laptop or notebook computers, distributed computer systems, computing grids, or servers.

Platforms, systems, and methods disclosed herein can comprise a mobile device comprising a computer system 100, e.g., for use in implementing a mobile device application (e.g., healthcare provider application). A mobile device can comprise a cellular phone (e.g., a smartphone), a tablet computer, a laptop computer, a personal digital assistant (PDA), or a handheld scanner.

Computer system 100 includes one or more processor(s) 101 (e.g., central processing units (CPUs), general purpose graphics processing units (GPGPUs), or quantum processing units (QPUs)) that carry out functions. Processor(s) 101 optionally contains a cache memory unit 102 for temporary local storage of instructions, data, or computer addresses. Processor(s) 101 are configured to assist in execution of computer readable instructions. Computer system 100 may provide functionality for the components depicted in FIG. 1 as a result of the processor(s) 101 executing non-transitory, processor-executable instructions embodied in one or more tangible computer-readable storage media, such as memory 103, storage 108, storage devices 135, and/or storage medium 136. The computer-readable media may store software that implements particular embodiments, and processor(s) 101 may execute the software. Memory 103 may read the software from one or more other computer-readable media (such as mass storage device(s) 135, 136) or from one or more other sources through a suitable interface, such as network interface 120. The software may cause processor(s) 101 to carry out one or more processes or one or more steps of one or more processes described or illustrated herein. Carrying out such processes or steps may include defining data structures stored in memory 103 and modifying the data structures as directed by the software.

The memory 103 may include various components (e.g., machine readable media) including, but not limited to, a random access memory component (e.g., RAM 104) (e.g., static RAM (SRAM), dynamic RAM (DRAM), ferroelectric random access memory (FRAM), phase-change random access memory (PRAM), etc.), a read-only memory component (e.g., ROM 105), and any combinations thereof. ROM 105 may act to communicate data and instructions unidirectionally to processor(s) 101, and RAM 104 may act to communicate data and instructions bidirectionally with processor(s) 101. ROM 105 and RAM 104 may include any suitable tangible computer-readable media described below. In one example, a basic input/output system 106 (BIOS), including basic routines that help to transfer information between elements within computer system 100, such as during start-up, may be stored in the memory 103.

Fixed storage 108 is connected bidirectionally to processor(s) 101, optionally through storage control unit 107. Fixed storage 108 provides additional data storage capacity and may also include any suitable tangible computer-readable media described herein. Storage 108 may be used to store operating system 109, executable(s) 110, data 111, applications 112 (application programs), and the like. Storage 108 can also include an optical disk drive, a solid-state memory device (e.g., flash-based systems), or a combination of any of the above. Information in storage 108 may, in appropriate cases, be incorporated as virtual memory in memory 103.

In one example, storage device(s) 135 may be removably interfaced with computer system 100 (e.g., via an external port connector (not shown)) via a storage device interface 125. Particularly, storage device(s) 135 and an associated machine-readable medium may provide non-volatile and/or volatile storage of machine-readable instructions, data structures, program modules, and/or other data for the computer system 100. In one example, software may reside, completely or partially, within a machine-readable medium on storage device(s) 135. In another example, software may reside, completely or partially, within processor(s) 101.

Bus 140 connects a wide variety of subsystems. Herein, reference to a bus may encompass one or more digital signal lines serving a common function, where appropriate. Bus 140 may be any of several types of bus structures including, but not limited to, a memory bus, a memory controller, a peripheral bus, a local bus, and any combinations thereof, using any of a variety of bus architectures. As an example and not by way of limitation, such architectures include an Industry Standard Architecture (ISA) bus, an Enhanced ISA (EISA) bus, a Micro Channel Architecture (MCA) bus, a Video Electronics Standards Association local bus (VLB), a Peripheral Component Interconnect (PCI) bus, a PCI-Express (PCI-X) bus, an Accelerated Graphics Port (AGP) bus, HyperTransport (HTX) bus, serial advanced technology attachment (SATA) bus, and any combinations thereof.

Computer system 100 may also include an input device 133. In one example, a user of computer system 100 may enter commands and/or other information into computer system 100 via input device(s) 133. Examples of an input device(s) 133 include, but are not limited to, an alpha-numeric input device (e.g., a keyboard), a pointing device (e.g., a mouse or touchpad), a touchpad, a touch screen, a multi-touch screen, a joystick, a stylus, a gamepad, an audio input device (e.g., a microphone, a voice response system, etc.), an optical scanner, a video or still image capture device (e.g., a camera), and any combinations thereof. For example, a mobile device (e.g., comprising a computer system 100) can comprise an imaging device (e.g., which can comprise an optical scanner and/or a video or still image capture device, such as a camera, or a combination thereof), which can comprise a means of acquiring optical data (e.g., via a lens or detector). A mobile device can comprise a light source, which may be operated by the mobile device application to improve lighting on a patient identifier target in some embodiments, for example, during use of an imaging device of the mobile device. In some cases, an input device 133 of a mobile device comprising a computing system 100 can comprise a keypad (e.g., wherein the keypad comprises physical keys). In some embodiments, the input device is a Kinect, Leap Motion, or the like. Input device(s) 133 may be interfaced to bus 140 via any of a variety of input interfaces 123 (e.g., input interface 123) including, but not limited to, serial, parallel, game port, USB, FIREWIRE, THUNDERBOLT, or any combination of the above.

In particular embodiments, when computer system 100 is connected to network 130, computer system 100 may communicate with other devices, specifically mobile devices and enterprise systems, distributed computing systems, cloud storage systems, cloud computing systems, and the like, connected to network 130. Communications to and from computer system 100 may be sent through network interface 120. For example, network interface 120 may receive incoming communications (such as requests or responses from other devices) in the form of one or more packets (such as Internet Protocol (IP) packets) from network 130, and computer system 100 may store the incoming communications in memory 103 for processing. Computer system 100 may similarly store outgoing communications (such as requests or responses to other devices) in the form of one or more packets in memory 103 and communicated to network 130 from network interface 120. Processor(s) 101 may access these communication packets stored in memory 103 for processing.

Examples of the network interface 120 include, but are not limited to, a network interface card, a modem, and any combination thereof. Examples of a network 130 or network segment 130 include, but are not limited to, a distributed computing system, a cloud computing system, a wide area network (WAN) (e.g., the Internet, an enterprise network), a local area network (LAN) (e.g., a network associated with an office, a building, a campus or other relatively small geographic space), a telephone network, a direct connection between two computing devices, a peer-to-peer network, and any combinations thereof. A network, such as network 130, may employ a wired and/or a wireless mode of communication. In general, any network topology may be used.

Information and data can be displayed through a display 132. In some cases, a mobile device (e.g., comprising a computer system 100) can comprise a display, which may be used to display acquired data (e.g., patient identifiers acquired via a camera of the mobile device), to display data from a viewfinder (e.g., to assist in positioning of the mobile device relative to a patient identifier target during acquisition of patient identifier data, for example, using optical data from the camera of the mobile device), and/or to display information via a user interface of the mobile device application. Examples of a display 132 include, but are not limited to, a cathode ray tube (CRT), a liquid crystal display (LCD), a thin film transistor liquid crystal display (TFT-LCD), an organic liquid crystal display (OLED) such as a passive-matrix OLED (PMOLED) or active-matrix OLED (AMOLED) display, a plasma display, and any combinations thereof. The display 132 can interface to the processor(s) 101, memory 103, and fixed storage 108, as well as other devices, such as input device(s) 133, via the bus 140. The display 132 is linked to the bus 140 via a video interface 122, and transport of data between the display 132 and the bus 140 can be controlled via the graphics control 121. In some embodiments, the display is a video projector. In some embodiments, the display is a head-mounted display (HMD) such as a VR headset. In further embodiments, suitable VR headsets include, by way of non-limiting examples, HTC Vive, Oculus Rift, Samsung Gear VR, Microsoft HoloLens, Razer OSVR, FOVE VR, Zeiss VR One, Avegant Glyph, Freefly VR headset, and the like. In still further embodiments, the display is a combination of devices such as those disclosed herein.

In addition to a display 132, computer system 100 may include one or more other peripheral output devices 134 including, but not limited to, an audio speaker, a printer, a storage device, and any combinations thereof. Such peripheral output devices may be connected to the bus 140 via an output interface 124. Examples of an output interface 124 include, but are not limited to, a serial port, a parallel connection, a USB port, a FIREWIRE port, a THUNDERBOLT port, and any combinations thereof.

In addition or as an alternative, computer system 100 may provide functionality as a result of logic hardwired or otherwise embodied in a circuit, which may operate in place of or together with software to execute one or more processes or one or more steps of one or more processes described or illustrated herein. Reference to software in this disclosure may encompass logic, and reference to logic may encompass software. Moreover, reference to a computer-readable medium may encompass a circuit (such as an IC) storing software for execution, a circuit embodying logic for execution, or both, where appropriate. The present disclosure encompasses any suitable combination of hardware, software, or both.

Those of skill in the art will appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality.

The various illustrative logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the embodiments disclosed herein may be embodied directly in hardware, in a software module executed by one or more processor(s), or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

In accordance with the description herein, suitable computing devices include, by way of non-limiting examples, server computers, desktop computers, laptop computers, notebook computers, handheld computers, Internet appliances, mobile smartphones, and tablet computers. Those of skill in the art will also recognize that select televisions, video players, and digital music players with optional computer network connectivity are suitable for use in the system described herein. Suitable tablet computers, in various embodiments, include those with booklet, slate, and convertible configurations, known to those of skill in the art.

In some embodiments, the computing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smartphone operating systems include, by way of non-limiting examples, Nokia® Symbian® OS, Apple® iOS®, Research In Motion® BlackBerry OS®, Google® Android®, Microsoft® WindowsPhone® OS, Microsoft® WindowsMobile® OS, Linux®, and Palm® WebOS®.

Non-Transitory Computer Readable Storage Medium

In some embodiments, the platforms, systems, media, and methods disclosed herein include one or more non-transitory computer readable storage media encoded with a program including instructions executable by the operating system of an optionally networked computing device. For example, a mobile device can comprise a computer system 100 and a non-transitory memory on which are stored instructions that when executed implement (e.g., instantiate and/or run) a mobile device application on the mobile device and/or operate additional functionalities of the mobile device, such as an imaging device of the mobile device (e.g., a camera), a display of the mobile device, and/or a wireless communication system of the mobile device, one or more of which may interface with and/or be controlled by the mobile device application, in various embodiments. In further embodiments, a computer readable storage medium is a tangible component of a computing device. In still further embodiments, a computer readable storage medium is optionally removable from a computing device. In some embodiments, a computer readable storage medium includes, by way of non-limiting examples, CD-ROMs, DVDs, flash memory devices, solid state memory, magnetic disk drives, magnetic tape drives, optical disk drives, distributed computing systems including cloud computing systems and services, and the like. In some cases, the program and instructions are permanently, substantially permanently, semi-permanently, or non-transitorily encoded on the media.

Computer Program

In some embodiments, the platforms, systems, media, and methods disclosed herein include at least one computer program, or use of the same. A computer program includes a sequence of instructions, executable by one or more processor(s) of the computing device's CPU, written to perform a specified task. Computer readable instructions may be implemented as program modules, such as functions, objects, Application Programming Interfaces (APIs), computing data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

Mobile Application

In some embodiments, a computer program includes a mobile application provided to a mobile computing device. In some embodiments, the mobile application is provided to a mobile computing device at the time it is manufactured. In other embodiments, the mobile application is provided to a mobile computing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C#, Objective-C, Java™, JavaScript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Web Application

In some embodiments, a computer program includes a web application. In light of the disclosure provided herein, those of skill in the art will recognize that a web application, in various embodiments, utilizes one or more software frameworks and one or more database systems. In some embodiments, a web application is created upon a software framework such as Microsoft® .NET or Ruby on Rails (RoR). In some embodiments, a web application utilizes one or more database systems including, by way of non-limiting examples, relational, non-relational, object oriented, associative, XML, and document oriented database systems. In further embodiments, suitable relational database systems include, by way of non-limiting examples, Microsoft® SQL Server, mySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). In some embodiments, a web application is written to some extent in a client-side scripting language such as Asynchronous JavaScript and XML (AJAX), Flash® ActionScript, JavaScript, or Silverlight. In some embodiments, a web application is written to some extent in a server-side coding language such as Active Server Pages (ASP), ColdFusion, Perl, Java™, JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM® Lotus Domino°. In some embodiments, a web application includes a media player element. In various further embodiments, a media player element utilizes one or more of many suitable multimedia technologies including, by way of non-limiting examples, Adobe® Flash®, HTML 5, Apple® QuickTime®, Microsoft® Silverlight®, Java™, and Unity®.

Software Modules

In some embodiments, the platforms, systems, media, and methods disclosed herein include software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, a distributed computing resource, a cloud computing resource, or combinations thereof. In further various embodiments, a software module comprises a plurality of files, a plurality of sections of code, a plurality of programming objects, a plurality of programming structures, a plurality of distributed computing resources, a plurality of cloud computing resources, or combinations thereof. In various embodiments, the one or more software modules comprise, by way of non-limiting examples, a web application, a mobile application, a standalone application, and a distributed or cloud computing application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on a distributed computing platform such as a cloud computing platform. In some embodiments, software modules are hosted on one or more machines in one location. In other embodiments, software modules are hosted on one or more machines in more than one location.

Databases

In some embodiments, the platforms, systems, media, and methods disclosed herein include one or more databases, or use of the same. In view of the disclosure provided herein, those of skill in the art will recognize that many databases are suitable for storage and retrieval of personal identification information (e.g., personal identifier data) and/or medical data associated with a patient's medical file (e.g., images, biographical information, and/or data comprising a diagnosis and/or a treatment) information. In various embodiments, suitable databases include, by way of non-limiting examples, relational databases, non-relational databases, object oriented databases, object databases, entity-relationship model databases, associative databases, XML databases, document oriented databases, and graph databases. Further non-limiting examples include SQL, PostgreSQL, MySQL, Oracle, DB2, Sybase, and MongoDB. In some embodiments, a database is Internet-based. In further embodiments, a database is web-based. In still further embodiments, a database is cloud computing-based. In a particular embodiment, a database is a distributed database. In other embodiments, a database is based on one or more local computer storage devices.

Certain Definitions

Unless otherwise defined, all technical terms used herein have the same meaning as commonly understood by one of ordinary skill in the art to which the present subject matter belongs.

As used in this specification and the appended claims, the singular forms "a," "an," and "the" include plural references unless the context clearly dictates otherwise. Any reference to "or" herein is intended to encompass "and/or" unless otherwise stated.

Reference throughout this specification to "some embodiments," "further embodiments," or "a particular embodiment," means that a particular feature, structure, or characteristic described in connection with the embodiment is included in at least one embodiment. Thus, the appearances of the phrase "in some embodiments," or "in further embodiments," or "in a particular embodiment" in various places throughout this specification are not necessarily all referring to the same embodiment. Furthermore, the particular features, structures, or characteristics may be combined in any suitable manner in one or more embodiments.

While preferred embodiments of the present subject matter have been shown and described herein, it will be obvious to those skilled in the art that such embodiments are provided by way of example only. Numerous variations, changes, and substitutions will now occur to those skilled in the art without departing from the present subject matter. It should be understood that various alternatives to the embodiments of the present subject matter described herein may be employed in practicing the present subject matter.

What is claimed is:

1. A platform providing an upgraded medical imaging system, the platform comprising:
   a) an electronic medical records system comprising a data store comprising a plurality of patient electronic medical records (EMRs) associated with a plurality of patients;
   b) an existing medical imaging system having no access to any unique patient identifiers associated with the plurality of patients;
   c) a mobile device provided with a healthcare provider application comprising:
      i) a scanning module configured to acquire a unique patient identifier associated with a respective patient in the plurality of patients;
      ii) an accessibility module configured to provide a healthcare provider accessibility display comprising the unique patient identifier on a screen of the mobile device; and
      iii) a front-end data quality module configured to transmit the unique patient identifier over a network; and
   d) a server provided with an interface application comprising:
      i) a back-end data quality module configured to receive the unique patient identifier over the network;
      ii) an imaging session module configured to perform operations comprising:
         1. creating an imaging session record using the unique patient identifier;
         2. receiving at least one medical image from the existing medical imaging system, and including the at least one medical image in the imaging session record to associate the at least one medical image with the unique patient identifier; and
         3. creating a medical imaging record based at least in part on the unique patient identifier and the at least one medical image; and
      iii) an EMR module configured to receive from the electronic medical records system a respective EMR in the plurality of EMRs that is associated with the respective patient corresponding to the unique patient identifier, and persist the medical imaging record to the respective EMR for the respective patient, thereby producing an integrated EMR for the respective patient,
   wherein the data store of the electronic medical records system is updated with the integrated EMR for the respective patient.

2. The platform of claim 1, wherein the data store comprises a database server.

3. The platform of claim 1, wherein the data store comprises a cloud data store.

4. The platform of claim 1, wherein the existing medical imaging system comprises an ultrasound device, an x-ray radiography device, a magnetic resonance imaging device, an endoscopy device, a thermography device, a photography device, an X-ray computed tomography (CT) device, a positron emission tomography (PET) device, a single-photon emission computed tomography (SPECT) device, a photoacoustic imaging device, or a combination thereof.

5. The platform of claim 4, wherein the existing medical imaging system is DICOM-enabled.

6. The platform of claim 1, wherein the healthcare provider application comprises a front-end medical imaging workflow application.

7. The platform of claim 6, wherein the healthcare provider application is implemented as a native mobile application.

8. The platform of claim 1, wherein the unique patient identifier comprises a text string, a number, a biometric feature of the patient, a linear barcode, a 2D barcode, or a combination thereof.

9. The platform of claim 1, wherein the healthcare provider application acquires the unique patient identifier using a camera of the mobile device.

10. The platform of claim 1, wherein the healthcare provider application further comprises a healthcare provider sign-in module configured to verify the identity of a healthcare provider operating the healthcare provider application.

11. The platform of claim 10, wherein a module of the interface application is configured to transmit the medical imaging record to the healthcare provider.

12. The platform of claim 10, wherein a module of the interface application is configured to transmit the medical imaging record to a dedicated communication server.

13. The platform of claim 1, wherein a module of the interface application is configured to use the unique patient identifier to retrieve patient information from the electronic medical records system.

14. The platform of claim 1, further comprising a back-end medical imaging workflow application.

15. The platform of claim 14, wherein the back-end medical imaging workflow application is implemented as a cloud application.

16. The platform of claim 1, wherein neither the mobile device nor the healthcare provider application communicates directly with the existing medical imaging system.

17. The platform of claim 1, configured to provide the upgraded medical imaging system without modifying the existing medical imaging system.

18. The platform of claim 1, wherein the front-end data quality module is further configured to initiate an EMR query.

19. The platform of claim 18, wherein initiating an EMR query comprises transmitting an EMR query initiation signal to the server.

\* \* \* \* \*